United States Patent
Celeste et al.

(10) Patent No.: US 6,719,968 B2
(45) Date of Patent: *Apr. 13, 2004

(54) TENDON-INDUCING COMPOSITIONS

(75) Inventors: Anthony J. Celeste, Hudson, MA (US); John M. Wozney, Hudson, MA (US); Vicki A. Rosen, Brookline, MA (US); Neil M. Wolfman, Dover, MA (US); Gerald H. Thomsen, Port Jefferson, NY (US); Douglas A. Melton, Lexington, MA (US)

(73) Assignee: Genetics Institute, LLC., Cambridge, MA (US)

( * ) Notice: Subject to any disclaimer, the term of this patent is extended or adjusted under 35 U.S.C. 154(b) by 71 days.

This patent is subject to a terminal disclaimer.

(21) Appl. No.: 09/945,182

(22) Filed: Aug. 31, 2001

(65) Prior Publication Data

US 2002/0160494 A1 Oct. 31, 2002

Related U.S. Application Data

(60) Division of application No. 08/808,324, filed on Feb. 28, 1997, now Pat. No. 6,284,872, which is a division of application No. 08/362,670, filed on Dec. 22, 1994, now Pat. No. 5,658,882, which is a continuation-in-part of application No. 08/217,780, filed on Mar. 25, 1994, now abandoned, and a continuation-in-part of application No. 08/164,103, filed on Dec. 7, 1993, now abandoned, and a continuation-in-part of application No. 08/333,576, filed on Nov. 2, 1994, now Pat. No. 6,027,919.

(51) Int. Cl.[7] .............................................. A61K 45/00
(52) U.S. Cl. ........................... 424/85.1; 514/2; 514/12; 530/350; 530/351; 530/395; 530/397; 530/399
(58) Field of Search ................................. 530/350, 351, 530/395, 397, 399; 514/5, 12; 424/85.1

(56) References Cited

U.S. PATENT DOCUMENTS

| | | | |
|---|---|---|---|
| 4,294,753 A | 10/1981 | Urist | 260/112 |
| 4,419,446 A | 12/1983 | Howley et al. | 435/68 |
| 4,434,094 A | 2/1984 | Seyedin et al. | 260/112 |
| 4,563,350 A | 1/1986 | Nathan et al. | 424/95 |
| 4,627,982 A | 12/1986 | Seyedin et al. | 424/95 |
| 4,761,471 A | 8/1988 | Urist | 530/350 |
| 4,774,228 A | 9/1988 | Seyedin et al. | 514/21 |
| 4,774,322 A | 9/1988 | Seyedin et al. | 530/353 |
| 4,804,744 A | 2/1989 | Sen | 530/350 |
| 4,877,864 A | 10/1989 | Wang et al. | 530/324 |
| 4,968,590 A | 11/1990 | Kuberasampath et al. | 530/326 |
| 5,013,649 A | 5/1991 | Wang et al. | 435/69.1 |
| 5,106,748 A | 4/1992 | Wozney et al. | 435/252.3 |
| 5,108,922 A | 4/1992 | Wang et al. | 435/240.2 |
| 5,116,738 A | 5/1992 | Wang et al. | 435/69.1 |
| 5,141,905 A | 8/1992 | Rosen et al. | 435/69.1 |
| 5,168,050 A | 12/1992 | Hammonds, Jr. et al. | 435/69.1 |
| 5,187,076 A | 2/1993 | Wozney et al. | 435/69.1 |
| 5,447,725 A | 9/1995 | Damani et al. | 424/435 |
| 5,455,041 A | 10/1995 | Genco et al. | 424/435 |
| 5,658,882 A * | 8/1997 | Celeste et al. | |
| 5,986,058 A | 11/1999 | Lee et al. | 530/351 |
| 6,027,919 A * | 2/2000 | Celeste et al. | |
| 6,284,872 B1 * | 9/2001 | Celeste et al. | |

FOREIGN PATENT DOCUMENTS

| | | |
|---|---|---|
| CA | 2017466 | 5/1990 |
| EP | 0 177 343 A1 | 9/1986 |
| EP | 0 336 760 A2 | 10/1989 |
| EP | 0 409 472 A1 | 1/1991 |
| EP | 0 416 578 A2 | 3/1991 |
| WO | WO 84/01106 | 3/1984 |
| WO | WO 91/18047 | 11/1991 |
| WO | WO 91/18098 | 11/1991 |
| WO | WO 93/00050 | 1/1993 |
| WO | WO 93/00432 | 1/1993 |
| WO | WO 93/16099 | 8/1993 |
| WO | WO 95/01801 | 1/1995 |
| WO | WO 95/01802 | 1/1995 |

OTHER PUBLICATIONS

Ngo et al., 1994, The Protein Folding Problem and Tertiary Structure Prediction, Merz et al., eds., Birkhauser, Boston, pp. 492–495.*

Wells, 1990, Biochemistry 29:8509–8517.*

Bowie et al., "Deciphering the Message in Protein Sequences Tolerance to Amino Acid Substitutions," *Science*, 247:1306–1310 (1990).

Chang et al., "Cartilage–derived Morphogenetic Proteins," *J. Biol. Chem*, 269:28227–28234 (1994).

Dagert et al., "Prolonged Incubation in Calcium Chloride Improves the Competence of *Escherichia coli* Cells," *Gene*, 6:23 (1979).

Derynck et al., "Human transforming growth factor–β complementary DNA sequence and expression in normal and transformed cells," *Nature*, 316:701 (1985).

Gentry et al., "Molecular Events in the Processing of Recombinant Type 1 Pre–Pro Transforming Growth Factor Beta to the Mature Polypeptide," *Molec. & Cell. Biol.*, 8:4162 (1988).

Gething et al., "Cell–surface expression of influenza haemagglutinin from a cloned DNA copy of the RNA gene," *Nature*, 293:620–625 (1981).

Gough et al., "Structure and expression of the mRNA for murine granulocyte–macrophage colony stimulating factor," *The EMBO Journal*, 4(3):645–653 (1985).

Ham et al., "Tendons, Ligaments, and Cartilage," *Histology*, JB Lippincott Co., pp. 367–369 (1979).

(List continued on next page.)

Primary Examiner—Elizabeth Kemmerer
(74) Attorney, Agent, or Firm—Finnegan, Henderson, Farabow, Garrett & Dunner LLP.

(57) ABSTRACT

Compositions of proteins with tendon/ligament-like tissue inducing activity are disclosed. The compositions are useful in the treatment of tendinitis and tendon or ligament defects and in related tissue repair.

4 Claims, 1 Drawing Sheet

OTHER PUBLICATIONS

Jang et al., "Initiation of Protein Synthesis by Internal Entry of Ribosomes into the 5' Nontranslated Region of Encephalomyocarditis Virus RNA In Vivo," *J. of Virology*, 63(4):1651–1660 (1989).

Joyce et al., "Tendon adhesion formation is stimulated by exogenous growth factors," *J. Cell Biol.*, 17E (Suppl), 136:Abstract R504 (1993).

Kaufman et al., "Coamplification and Coexpression of Human Tissue–Type Plasminogen Activator and Murine Dihydrofolate Reductase Sequences in Chinese Hamster Ovary Cells," *Mol. Cell. Biol.*, 5(7):1750–1759 (1985).

Kaufman,, "Identification of the components necessary for adenovirus translational control and their utilization in cDNA expression vectors," *Proc. Natl. Acad. Sci. USA*, 82:689–693 (1985).

Kaufman, et al., "Improved vectors for stable expression of foreign genes in mammalian cells by use of the untranslated leader sequence from EMC virus," *Nucl. Acids Res.*, 19(16):4485–4490 (1991).

Kaufman et al., "Construction of a Modular Dihydrofolate Reductase cDNA Gene: Analysis of Signals Utilized for Efficient Expression," *Mol. Cell Biol.*, 2: 1304–1319 (1982).

Laemmli, U.K., "Cleavage of Structural Proteins during the Assembly of the Head of Bacteriophage T4," *Nature*, 227:680–685 (1970).

LaVallie et al., "A Thioredoxin Gene Fusion Expression System that Circumvents Inclusion Body Formation in the *E. coli* Cytoplasm," *Bio/Technology*, 11:187–193 (1993).

Maniatis et al., Molecular Cloning (A Laboratory Manual), Cold Spring Harbor Laboratory, pp. 387–389 (1982).

Miller, et al., "An Insect Baculovirus Host–Vector System for High–Level Expression of Foreign Genes," *Genetic Engineering: Principles and Methods*, 8:277–298 (1986).

Miller, "Experiments in Molecular Genetics," Cold Spring Harbor Laboratory, New York, 1972.

Morinaga et al., "Improvement of Oligonucleotide–directed Site-specific Mutagenesis using Double–stranded Plasmid DNA," *Biotechnology*, 84:636 (1984).

Ngo et al., "Computational Complexity, Protein Structure Prediction, and the Levinthal Paradox," The Protein Folding Problem and Tertiary Structure Prediction, Merz et al., eds., Birkhauser, Boston, pp. 491–495 (1994).

Norrander et al., "Construction of improved M13 vectors using oligodeoxynucleotide–directed mutagenesis," *Gene*, 26:101–106 (1983).

Oakley, et al., "A Simplified Ultrasensitive Silver Stain for Detecting Proteins in Polyacrylamide Gels," *Analytical Biochemistry*, 105:361–363 (1980).

Okayama, et al., "High–Efficiency Cloning of Full–Length cDNA," *Mol. Cell. Biol.*, 2(2):161–170 (1982).

Ozkaynak et al., "OP–1 cDNA encodes an osteogenic protein in the TGF–β family," *EMBO J.*, 9(7):2085–2093 (1990).

Sampath et al., "Homology of bone–inductive proteins from human, monkey, bovine, and rat extracellular matrix," PNAS, 80:6591–6595 (1983).

Sampath et al., "Isolation of osteogenin, an extracellular matrix–associated, bone–inductive protein, by heparin affinity chromatography," PNAS, 84:7109–7113 (1987).

Sanger et al., "Nucleotide Sequence of Bacteriophage λ DNA," J. Mol. Biol., 162:729–773 (1982).

Storm et al., "Limb alterations in *brachypodism* mice due to mutations in a new member of the TGFα–superfamily," Nature, 368:639–642 (1994).

Takagi et al., "Cloning and nucleotide sequence of the aspartase gene of *Escherichia coli*" Nucl. Acids Res., 13:2063–2074 (1985).

Taniguchi et al., "Expression of the human fibroblast interferon gene in *Escherichia coli*," *Proc. Natl. Acad. Sci. USA*, 77(9):5230–5233 (1980).

Towbin et al., "Electrophoretic transfer of proteins from polyacrylamide gels to nitrocellulose sheets: Procedure and some applications," PNAS, 76(9):4350–4354 (1979).

Urist et al., "Bone Cell Differentiation and Growth Factors," Science, 220:680–686 (1983).

Wells, "Additivity of Mutational Effects in Proteins," in *Perspectives in Biochemistry*, 29:8509–8517 (1990).

Wong, et al., "Human GM–CSF: Molecular Cloning of the Complementary DNA and Purification of the Natural and Recombinant Proteins," *Science*, 228:810–815 (1985).

Wozney, "The Bone Morphogenetic Protein Family and Osteogenesis," *Molecular Reproduction and Development*, 32:160–167 (1992).

Wozney, "Bone Morphogenetic Proteins," *Progress in Growth Factor Research*, 1:267–280 (1989).

* cited by examiner

FIGURE 1

COMPARISON OF HUMAN V1-1 VS. HUMAN MP-52

```
V1-1   Ser Arg Cys Ser Arg Lys Pro Leu His Val Asp Phe Lys Glu Leu
  1    AGC CGC TGC AGC CGC AAG CCG TTG CAC GTG GAC TTC AAG GAG CTC
       ||| ||| ||  ||  ||| |   || || || ||  || ||| ||| ||  |
MP52   GCT CGC TGC AGT CGG AAG GCA CTG CAT GTC AAC TTC AAG GAC ATG
  1    Ala Arg Cys Ser Arg Lys Ala Leu His Val Asn Phe Lys Asp Met

16    Gly Trp Asp Asp Trp Ile Ile Ala Pro Leu Asp Tyr Glu Ala Tyr
 46    GGC TGG GAC GAC TGG ATC ATC GCG CCG CTG GAC TAC GAG GCG TAC
       ||| ||| ||| ||| ||| ||| ||| ||  ||  ||  ||  ||| ||| ||  | |
 46    GGC TGG GAC GAC TGG ATC ATC GCA CCC CTT GAG TAC GAG GCT TTC
 16    Gly Trp Asp Asp Trp Ile Ile Ala Pro Leu Glu Tyr Glu Ala Phe

31    His Cys Glu Gly Leu Cys Asp Phe Pro Leu Arg Ser His Leu Glu
 91    CAC TGC GAG GGC CTT TGC GAC TTC CCT TTG CGT TCG CAC CTC GAG
       ||| ||| ||  ||  ||| ||  ||| ||  ||| || || ||| || ||| ||| |||
 91    CAC TGC GAG GGG CTG TGC GAG TTC CCA TTG CGC TCC CAC CTG GAG
 31    His Cys Glu Gly Leu Cys Glu Phe Pro Leu Arg Ser His Leu Glu

46    Pro Thr Asn His Ala Ile Ile Gln Thr Leu Leu Asn Ser Met Ala
121    CCC ACC AAC CAT GCC ATC ATT CAG ACG CTG CTC AAC TCC ATG GCA
       ||| ||  ||  ||| ||  ||  ||  ||| ||  |||  |  ||| ||| ||| |
121    CCC ACG AAT CAT GCA GTC ATC CAG ACC CTG ATG AAC TCC ATG GAC
 46    Pro Thr Asn His Ala Val Ile Gln Thr Leu Met Asn Ser Met Asp

61    Pro Asp Ala Ala Pro Ala Ser Cys Cys Val Pro Ala Arg Leu Ser
181    CCA GAC GCG GCG CCG GCC TCC TGC TGT GTG CCA GCG CGC CTC AGC
       ||  ||   |   |  ||  ||  || ||| ||| ||| ||  || ||  ||  ||
181    CCC GAG TCC ACA CCA CCC ACC TGC TGT GTG CCC ACG CGG CTG AGT
 61    Pro Glu Ser Thr Pro Pro Thr Cys Cys Val Pro Thr Arg Leu Ser

76    Pro Ile Ser Ile Leu Tyr Ile Asp Ala Ala Asn Asn Val Val Tyr
226    CCC ATC AGC ATC CTC TAC ATC GAC GCC GCC AAC AAC GTT GTC TAC
       ||| ||| ||| ||| ||| |  || ||| |   ||| ||| ||  ||  | |
226    CCC ATC AGC ATC CTC TTC ATT GAC TCT GCC AAC AAC GTG GTG TAT
 76    Pro Ile Ser Ile Leu Phe Ile Asp Ser Ala Asn Asn Val Val Tyr

91    Lys Gln Tyr Glu Asp Met Val Val Glu Ala Cys Gly Cys Arg
271    AAG CAA TAC GAG GAC ATG GTG GTG GAG GCC TGC GGC TGC AGG
       ||| ||  ||  ||| ||| ||| ||  ||| ||| |   || ||| ||| |||
271    AAG CAG TAT GAG GAC ATG GTC GTG GAG TCG TGT GGC TGC AGG
 91    Lys Gln Tyr Glu Asp Met Val Val Glu Ser Cys Gly Cys Arg
```

Homology at the nucleotide level: 249/312 = 79.8%
Homology at the amino acid level: 84/104 = 80.8%

TENDON-INDUCING COMPOSITIONS

RELATED APPLICATIONS

This application is a division of U.S. application Ser. No. 08/808,324, filed Feb. 28, 1997, which issued as U.S. Pat. No. 6,284,872, on Sep. 4, 2001; which is a division of U.S. application Ser. No. 08/362,670, filed Dec. 22, 1994, which issued as U.S. Pat. No. 5,658,882, on Aug. 19, 1997; which is a continuation-in-part of U.S. application Ser. No. 08/217,780, filed Mar. 25, 1994, now abandoned, U.S. application Ser. No. 08/164,103, filed Dec. 7, 1993, now abandoned, and U.S. application Ser. No. 08/333,576, filed Nov. 2, 1994, which issued as U.S. Pat. No. 6,027,919, on Feb. 22, 2000.

FIELD OF THE INVENTION

The present invention relates to a novel family of purified proteins, and compositions containing such proteins, which compositions are useful for the induction of tendon/ligament-like tissue formation, wound healing and ligament and other tissue repair. These proteins may also be used in compositions for augmenting the activity of bone morphogenetic proteins.

BACKGROUND OF THE INVENTION

The search for the molecule or molecules responsible for formation of bone, cartilage, tendon and other tissues present in bone and other tissue extracts has led to the discovery of a novel set of molecules called the Bone Morphogenetic Proteins (BMPs). The structures of several proteins, designated BMP-1 through BMP-11, have previously been elucidated. The unique inductive activities of these proteins, along with their presence in bone, suggests that they are important regulators of bone repair processes, and may be involved in the normal maintenance of bone tissue. There is a need to identify additional proteins which play a role in forming other vital tissues. The present invention relates to the identification of a family of proteins, which have tendon/ligament-like tissue inducing activity, and which are useful in compositions for the induction of tendon/ligament-like tissue formation and repair.

SUMMARY OF THE INVENTION

In one embodiment, the present invention comprises DNA molecules encoding a tendon/ligament-like inducing protein which the inventors have named V1-1. This novel protein is now called BMP-12. The present invention also includes DNA molecules encoding BMP-12 related proteins.

BMP-12 related proteins are a subset of the BMP/TGF-β/Vg-1 family of proteins, including BMP-12 and VL-1, which are defined as tendon/ligament-like tissue inducing proteins encoded by DNA sequences which are cloned and identified, e.g., using PCR, using BMP-12 specific primers, such as primers #6 and #7 described below, with reduced stringency conditions. It is preferred that the DNA sequences encoding BMP-12 related proteins share at least about 80% homology at the amino acid level from amino acids with amino acids #3 to #103 of SEQ ID NO:1.

The DNA molecules preferably have a DNA sequence encoding the BMP-12 protein, the sequence of which is provided in SEQ ID NO:1, or a BMP-12 related protein as further described herein. Both the BMP-12 protein and BMP-12 related proteins are characterized by the ability to induce the formation of tendon/ligament-like tissue in the assay described in the examples.

The DNA molecules of the invention preferably comprise a DNA sequence, as described in SEQUENCE ID NO:1; more preferably nucleotides #496 to #882, #571 to #882 or #577 to #882 of SEQ ID NO:1; or DNA sequences which hybridize to the above under stringent hybridization conditions and encode a protein which exhibits the ability to form tendon/ligament-like tissue. The DNA molecules of the invention may also comprise a DNA sequence as described in SEQ ID NO:25; more preferably nucleotides #604 or #658 to #964 of SEQ ID NO:25.

The DNA molecules of the invention also include DNA molecules comprising a DNA sequence encoding a BMP-12 related protein with the amino acid sequence shown in SEQ ID NO:2 or SEQ ID NO:26, as well as naturally occurring allelic sequences and equivalent degenerative codon sequences of SEQ ID NO:2 or SEQ ID NO:26. Preferably, the DNA sequence of the present invention encodes amino acids #-25 to #104, #1 to #104 or #3 to #103 of SEQ ID NO:2; or amino acids #1 to #120 or #19 to #120 of SEQ ID NO:26. The DNA sequence may comprise, in a 5' to 3' direction, nucleotides encoding a propeptide, and nucleotides encoding for amino acids #-25 to #104, #1 to #104 or #3 to #103 of SEQ ID NO:2; or amino acids #1 to #120 or #19 to #120 of SEQ ID NO:26 The propeptide useful in the above embodiment is preferably selected from the group consisting of native BMP-12 propeptide and a protein propeptide from a different member of the TGF-B superfamily or BMP family. The invention further comprises DNA sequences which hybridize to the above DNA sequences under stringent hybridization conditions and encode a BMP-12 related protein which exhibits the ability to induce formation of tendon/ligament-like tissue.

In other embodiments, the present invention-comprises host cells and vectors which comprise a DNA molecule encoding the BMP-12 protein, or a BMP-12 related protein. The host cells and vectors may further comprise the coding sequence in operative association with an expression control sequence therefor.

In another embodiment, the present invention comprises a method for producing a purified BMP-12 related protein, said method comprising the steps of culturing a host cell transformed with the above DNA molecule or vector comprising a nucleotide sequence encoding a BMP-12 related protein; and (b) recovering and purifying said BMP-12 related protein from the culture medium. In a preferred embodiment, the method comprises (a) culturing a cell transformed with a DNA molecule comprising the nucleotide sequence from nucleotide #496, #571 or #577 to #879 or #882 as shown in SEQ ID NO:1; or the nucleotide sequence from #604 or #658 to #963 of SEQ ID NO:25; and (b) recovering and purifying from said culture medium a protein comprising the amino acid sequence from amino acid #-25, #1 or #3 to amino acid #103 or #104 as shown in SEQ ID NO:2; or from amino acid #1 or #19 to amino acid #120 as shown in SEQ ID NO:26. The present invention also includes a purified protein produced by the above methods.

The present invention further comprises purified BMP-12 related protein characterized by the ability to induce the formation of tendon/ligament-like tissue. The BMP-12 related polypeptides preferably comprise an amino acid sequence as shown in SEQ ID NO:2. The polypeptide more preferably comprise amino acids #-25, #1 or #3 to #103 or #104 as set forth in SEQ ID NO:2; or amino acids #1 or #19 to #120 as set forth in SEQ ID NO:26. In a preferred embodiment, the purified polypeptide may be in the form of a dimer comprised of two subunits, each with the amino acid sequence of SEQ ID NO:2.

In another embodiment, the present invention comprises compositions comprising an effective amount of the above-described BMP-12 related proteins. In the compositions, the protein may be admixed with a pharmaceutically acceptable vehicle.

The invention also includes methods for tendon/ligament-like tissue healing and tissue repair, for treating tendinitis, or other tendon or ligament defects, and for inducing tendon/ligament-like tissue formation in a patient in need of same, comprising administering to said patient an effective amount of the above composition.

Other embodiments include chimeric DNA molecules comprising a DNA sequence encoding a propeptide from a member of the TGF-β superfamily of proteins linked in correct reading frame to a DNA sequence encoding a BMP-12 related polypeptide. One suitable propeptide is the propeptide from BMP-2. The invention also includes heterodimeric protein molecules comprising one monomer having the amino acid sequence shown in SEQ ID NO:2, and one monomer having the amino acid sequence of another protein of the TGF-β subfamily.

Finally, the present invention comprises methods for inducing tendon/ligament-like tissue formation in a patient in need of same comprising administering to said patient an effective amount of a composition comprising a protein which exhibits the ability to induce formation of tendon/ligament-like tissue, said protein having an amino acid sequence shown in SEQ ID NO:2 or SEQ ID NO:4 or SEQ ID NO:26. The amino acid sequences are more preferably one of the following: (a) amino acids #–25, #1 or #3 to #103 or #104 of SEQ ID NO:2; (b) amino acids #1 or #19 to #119 or #120 of SEQ ID NO:4; (c) amino acids #1 or #19 to #119 or #120 of SEQ ID NO:26; (d) mutants and/or variants of (a), (b) or (c) which exhibit the ability to form tendon and/or ligament. In other embodiments of the above method, the protein is encoded by a DNA sequence of SEQ ID NO:1, SEQ ID NO:3 or SEQ ID NO:25, more preferably one of the following: (a) nucleotides #496, #571 or #577 to #879 or #882 of SEQ ID NO:1; (b) nucleotides #845 or #899 to #1201 or #1204 of SEQ ID NO:3; (c) nucleotides #605 or #659 to #961 or #964 of SEQ ID NO:25; and (d) sequences which hybridize to (a) or (b) under stringent hybridization conditions and encode a protein which exhibits the ability to form tendon/ligament-like tissue.

Description of the Sequences

SEQ ID NO:1 is the nucleotide sequence encoding the human BMP-12.

SEQ ID NO:2 is the amino acid sequence comprising the mature human BMP-12 polypeptide.

SEQ ID NO:3 is the nucleotide sequence encoding the protein MP52.

SEQ ID NO:4 is the amino acid sequence, comprising the mature MP52 polypeptide.

SEQ ID NO:5 is the nucleotide sequence of a specifically amplified portion of the human BMP-12 encoding sequence.

SEQ ID NO:6 is the amino acid sequence encoded by the nucleotide sequence of SEQ ID NO:5.

SEQ ID NO:7 is the nucleotide sequence of a specifically amplified portion of the human VL-1 encoding sequence.

SEQ ID NO:8 is the amino acid sequence encoded by the nucleotide sequence of SEQ ID NO:7.

SEQ ID NO:9 is the nucleotide sequence of the plasmid pALV1-781, used for expression of BMP-12 in *E. coli*.

SEQ ID NO:10 is the nucleotide sequence of a fragment of the murine clone, mV1.

SEQ ID NO:11 is the amino acid sequence of a fragment of the murine protein encoded by mV1.

SEQ ID NO:12 is the nucleotide sequence of a fragment of the murine clone, mV2.

SEQ ID NO:13 is the amino acid sequence of a fragment of the murine protein encoded by mV2.

SEQ ID NO:14 is the nucleotide sequence of a fragment of the murine clone, mV9.

SEQ ID NO:15 is the amino acid sequence of a fragment of the murine protein encoded by mV9.

SEQ ID NO:16 is the amino acid sequence of a BMP/TGF-β/Vg-1 protein consensus sequence The first Xaa represents either Gln or Asn; the second Xaa represents either Val or Ile.

SEQ ID NO:17 is the nucleotide sequence of oligonucleotide #1.

SEQ ID NO:18 is the amino acid sequence of a BMP/TGF-β/Vg-1 protein consensus sequence. The Xaa represents either Val or Leu.

SEQ ID NO:19 is the nucleotide sequence of oligonucleotide #2.

SEQ ID NO:20 is the nucleotide sequence of oligonucleotide #3.

SEQ ID NO:21 is the nucleotide sequence of oligonucleotide #4.

SEQ ID NO:22 is the nucleotide sequence of oligonucleotide #5.

SEQ ID NO:23 is the nucleotide sequence of oligonucleotide #6.

SEQ ID NO:24 is the nucleotide sequence of oligonucleotide #7.

SEQ ID NO:25 is the nucleotide sequence of the human VL-1 (BMP-13) encoding sequence.

SEQ ID NO:26 is the amino acid sequence encoded by the nucleotide sequence of SEQ ID NO:25.

SEQ ID NO:27 is the nucleotide sequence encoding a fusion of BMP-2 propeptide and the mature coding sequence of BMP-12.

SEQ ID NO:28 is the amino acid sequence encoded by the nucleotide sequence of SEQ ID NO:27.

SEQ ID NO:29 is the nucleotide sequence encoding the murine mV1 protein. the first Xaa is Val, Ala, Glu or Gly; the second Xaa is Ser, Pro Thr or Ala; the third Xaa is Ser or Arg; the fourth Xaa is Leu, Pro, Gln or Arg; the fifth Xaa is Cys or Trp; the sixth Xaa is Val, Ala, Asp or Gly; the seventh Xaa is Val, Ala, Glu or Gly; the eigth Xaa is Gln, Lys or Glu.

SEQ ID NO:30 is the amino acid sequence encoded by the nucleotide sequence of SEQ ID NO:29. the first Xaa through the eigth Xaa are the same as in SEQ ID NO:29.

SEQ ID NO:31 is the nucleotide sequence encoding the murine mV2 protein. the first Xaa is Pro or Thr; the second Xaa is Val.

SEQ ID NO:32 is the amino acid sequence encoded by the nucleotide sequence of SEQ ID NO:31. The first Xaa and the second Xaa are the same as in SEQ ID NO:31.

SEQ ID NO:33 is the nucleotide sequence encoding human BMP-12 protein.

SEQ ID NO:34 is the amino acid sequence encoded by the nucleotide sequence of SEQ ID NO:33.

SEQ ID NO:35 is the nucleotide sequence of oligonucleotide #8.

BRIEF DESCRIPTION OF THE FIGURES

FIG. 1 is a comparison of the human BMP-12 and human MP52 sequences. The sequence of human BMP-12 is set forth in SEQ ID NO: 1. The sequence of MP52 is set forth in SEQ ID NO: 3.

DETAILED DESCRIPTION OF THE INVENTION

The DNA sequences of the present invention are useful for producing proteins which induce the formation of tendon/ligament-like tissue, as described further below. The DNA sequences of the present invention are further useful for isolating and cloning further DNA sequences encoding BMP-12 related proteins with similar activity. These BMP-12 related proteins may be homologues from other species, or may be related proteins within the same species.

Still, a further aspect of the invention are DNA sequences coding for expression of a tendon/ligament-like tissue inducing protein. Such sequences include the sequence of nucleotides in a 5' to 3' direction illustrated in SEQ ID NO:1 or SEQ ID NO:25, DNA sequences which, but for the degeneracy of the genetic code, are identical to the DNA sequence SEQ ID NO:1 or 25, and encode the protein of SEQ ID NO:2 or 26. Further included in the present invention are DNA sequences which hybridize under stringent conditions with the DNA sequence of SEQ ID NO:1 or 25 and encode a protein having the ability to induce the formation of tendon or ligament. Preferred DNA sequences include those which hybridize under stringent conditions as described in Maniatis et al, *Molecular Cloning* (*A Laboratory Manual*), Cold Spring Harbor Laboratory (1982), pages 387 to 389. Finally, allelic or other variations of the sequences of SEQ ID NO:1 or 25, whether such nucleotide changes result in changes in the peptide sequence or not, but where the peptide sequence still has tendon/ligament-like tissue inducing activity, are also included in the present invention.

The human BMP-12 DNA sequence (SEQ ID NO:1) and amino acid sequence (SEQ ID NO:2) are set forth in the Sequence Listings. Another protein that is useful for the compositions and methods of the present invention is VL-1. VL-1 is a BMP-12 related protein which was cloned using sequences from BMP-12. The inventors have now designated VL-1 as BMP-13. A partial DNA sequence of VL-1 (SEQ ID NO:7) and the encoded amino acid sequence (SEQ ID NO:8); as well as a DNA sequence encoding the mature VL-1 (SEQ ID NO:25) and the encoded amino acid sequence (SEQ ID NO:26) are set forth in the Sequence Listings. Although further descriptions are made with reference to the BMP-12 sequence of SEQ ID NO:1 and 2, it will be recognized that the invention includes similar modifications and improvements which may be made to other BMP-12 related sequences, such as the VL-1 sequence shown in SEQ ID NO:25 and 26.

The sequence of BMP-12 shown in SEQ ID NO. 1 includes the entire mature sequence and approximately 190 amino acids of the propeptide. The coding sequence of the mature human BMP-12 protein appears to begin at nucleotide #496 or #571 and continues through nucleotide #882 of SEQ ID NO:1. The first cysteine in the seven cysteine structure characteristic of TGF-β proteins begins at nucleotide #577. The last cysteine ends at #879. Thus, it is expected that DNA sequences encoding active BMP-12 species will comprise nucleotides #577 to #879 of SEQ ID NO:1.

It is expected that BMP-12, as expressed by mammalian cells such as CHO cells, exists as a heterogeneous population of active species of BMP-12 protein with varying N-termini. It is expected that all active species will contain the amino acid sequence beginning with the cysteine residue at amino acid #3 of SEQ ID NO:2 and continue through at least the cysteine residue at amino acid 103 or until the stop codon after amino acid 104. Other active species contain additional amino acid sequence in the N-terminal direction. As described further herein, the N-termini of active species produced by mammalian cells are expected to begin after the occurrence of a consensus cleavage site, encoding a peptide sequence Arg-X-X-Arg (SEQ ID NO:2, residues −4 to −1).

Thus, it is expected that DNA sequences encoding active BMP-12 proteins will have a nucleotide sequence comprising the nucleotide sequence beginning at any of nucleotides #196,199, 208, 217, 361, 388, 493, 496 or 571 to nucleotide #879 or 882 of SEQ ID NO:1.

The N-terminus of one active species of human BMP-12 has been experimentally determined by expression in *E. coli* to be as follows: [M]SRXSRKPLHVDF (SEQ ID NO:2, residues 1 to 12), wherein X designates an amino acid residue with no clear signal, which is consistent with a cysteine residue at that location. Thus, it appears that the N-terminus of this species of BMP-12 is at amino acid #1 of SEQ ID NO:1, and a DNA sequence encoding said species of BMP-12 would start at nucleotide #571 of SEQ ID NO:1. The apparent molecular weight of this species of human BMP-12 dimer was determined by SDS-PAGE to be approximately 20–22 kd on a Novex 16% tricine gel. The pl of this molecule is approximately 4.9. The human BMP-12 protein exists as a clear, colorless solution in 0.1% trifluoroacetic acid. The N-terminus of another active species of human BMP-12 has been experimentally determined by expression in *E. coli* to be [M]TALA (SEQ ID NO:2, residues −25 to −22). The pl of this molecule is approximately 7.0. The apparent molecular weight of this species of human BMP-12 dimer was determined by SDS-PAGE to be approximately 25–27 kd on a Novex 16% tricine gel. The human BMP-12 protein exists as a clear, colorless solution in 0.1% trifluoroacetic acid.

As described earlier, BMP-12 related proteins are a subset of the BMP/TGF-β/Vg-1 family of proteins, including BMP-12 and VL-1, which can be defined as tendon/ligament-like tissue inducing proteins encoded by DNA sequences which can be cloned and identified, e.g., using PCR, using BMP-12 specific primers, such as primers #6 and #7 described below, with reduced stringency conditions. It is preferred that DNA sequences of the present invention share at least about 80% homology at the amino acid level from amino acids with the DNA encoding amino acids #3 to #103 of SEQ ID NO:1. For the purposes of the present invention, the term BMP-12 related proteins does not include the human MP52 protein. Using the sequence information of SEQ ID NO:1 and SEQ ID NO:3, and the comparison provided in FIG. 1 it is within the skill of the art to design primers to the BMP-12 sequence which will allow for the cloning of genes encoding BMP-12 related proteins.

One example of the BMP-12-related proteins of the present invention is VL-1, presently referred to as BMP-13. The sequence of the full mature BMP-13 sequence and at least a part of the propeptide of BMP-13 is given in SEQ ID NO:25. Like BMP-12, it is expected that BMP-13, as expressed by mammalian cells such as CHO cells, exists as a heterogeneous population of active species of BMP-13 protein with varying N-termini. It is expected that all active species will contain the amino acid sequence beginning with the cysteine residue at amino acid #19 of SEQ ID NO:26 and continue through at least the cysteine residue at amino acid 119 or until the stop codon after amino acid 120. Other active species contain additional amino acid sequence in the N-terminal direction. As described further herein, the N-termini of active species produced by mammalian cells are expected to begin after the occurrence of a consensus cleavage site, encoding a peptide sequence Arg-X-X-Arg (SEQ ID NO:26, residues −4 to −1). Thus, it is expected that DNA sequences encoding active BMP-13 proteins will have a nucleotide sequence comprising the nucleotide sequence beginning at any of nucleotides #410, 458, 602, 605 or 659, to nucleotide #961 or 964 of SEQ ID NO:25.

In order to produce the purified tendon/ligament-like tissue inducing proteins useful for the present invention, a method is employed comprising culturing a host cell transformed with a DNA sequence comprising a suitable coding sequence, particularly the DNA coding sequence from nucleotide #496, #571 or #577 to #879 or #882 of SEQ ID NO:1; and recovering and purifying from the culture medium a protein which contains the amino acid sequence or a substantially homologous sequence as represented by amino acids #−25, #1 or #3 to #103 or #104 of SEQ ID NO:2. In another embodiment, the method employed comprises culturing a host cell transformed with a DNA sequence comprising a suitable coding sequence, particularly the DNA coding sequence from nucleotide #605 or #659 to #961 or #964 of SEQ ID NO:25; and recovering and purifying from the culture medium a protein which contains the amino acid sequence or a substantially homologous sequence as represented by amino acids #1 or #19 to #119 or #120 of SEQ ID NO:26.

The human MP52 DNA is described in WO93/16099, the disclosure of which is incorporated herein by reference. However, this document does not disclose the ability of the protein to form tendon/ligament-like tissue, or its use in compositions for induction of tendon/ligament-like tissue. Human MP52 was originally isolated using RNA from human embryo tissue. The human MP52 nucleotide sequence (SEQ ID NO:3) and the encoded amino acid sequences (SEQ ID NO:4) are set forth in the Sequence Listings herein. The MP52 protein appears to begin at nucleotide #845 of SEQ ID NO:3 and continues through nucleotide #1204 of SEQ ID NO:3. The first cysteine of the seven cysteine structure characteristic of TGF-β proteins begins at nucleotide #899. The last cysteine ends at #1201. Other active species of MP52 protein may have additional nucleotides at the N-terminal direction from nucleotide #845 of SEQ ID NO:3.

Purified human MP52 proteins of the present invention may be produced by culturing a host cell transformed with a DNA sequence comprising the DNA coding sequence of SEQ ID NO:3 from nucleotide #845 to #1204, and recovering and purifying from the culture medium a protein which contains the amino acid sequence or a substantially homologous sequence as represented by amino acids #1 to #120 of SEQ ID NO:4. It is also expected that the amino acid sequence from amino acids #17 or #19 to #119 or #120 of SEQ ID NO:4 will retain activity. Thus, the DNA sequence from nucleotides #845, #893 or #899 to #1201 or #1204 are expected to encode active proteins.

For expression of the protein in mammalian host cells, the host cell is transformed with a coding sequence encoding a propeptide suitable for the secretion of proteins by the host cell is linked in proper reading frame to the coding sequence for the mature protein. For example, see U.S. Pat. No. 5,168,050, the disclosure of which is hereby incorporated by reference, in which a DNA encoding a precursor portion of a mammalian protein other than BMP-2 is fused to the DNA encoding a mature BMP-2 protein. Thus, the present invention includes chimeric DNA molecules comprising a DNA sequence encoding a propeptide from a member of the TGF-β superfamily of proteins, is linked in correct reading frame to a DNA sequence encoding a tendon/ligament-like tissue inducing polypeptide. The term "chimeric" is used to signify that the propeptide originates from a different polypeptide than the encoded mature polypeptide. Of course, the host cell may be transformed with a DNA sequence coding sequence encoding the native propeptide linked in correct reading frame to a coding sequence encoding the mature protein shown in SEQ ID NO:2, SEQ ID NO:4, or SEQ ID NO:26. The full sequence of the native propeptide may be determined through methods known in the art using the sequences disclosed in SEQ ID NO:1, SEQ ID NO:3, or SEQ ID NO:25 to design a suitable probe for identifying and isolating the entire clone.

The present invention also encompasses the novel DNA sequences, free of association with DNA sequences encoding other proteinaceous materials, and coding for expression of tendon/ligament-like tissue inducing proteins. These DNA sequences include those depicted in SEQ ID NO:1 in a 5' to 3' direction and those sequences which hybridize thereto under stringent hybridization conditions [for example, 0.1×SSC, 0.1% SDS at 65° C.; see, T. Maniatis et al, *Molecular Cloning* (*A Laboratory Manual*), Cold Spring Harbor Laboratory (1982), pages 387 to 389] and encode a protein having tendon/ligament-like tissue inducing activity.

Similarly, DNA sequences which code for proteins coded for by the sequences of SEQ ID NO:1 or SEQ ID NO:25, or proteins which comprise the amino acid sequence of SEQ ID NO:2 or SEQ ID NO:26, but which differ in codon sequence due to the degeneracies of the genetic code or allelic variations (naturally-occurring base changes in the species population which may or may not result in an amino acid change) also encode the tendon/ligament-like tissue inducing proteins described herein. Variations in the DNA sequences of SEQ ID NO:1 or SEQ ID NO:25 which are caused by point mutations or by induced modifications (including insertion, deletion, and substitution) to enhance the activity, half-life or production of the polypeptides encoded are also encompassed in the invention.

Another aspect of the present invention provides a novel method for producing tendon/ligament-like tissue inducing proteins. The method of the present invention involves culturing a suitable cell line, which has been transformed with a DNA sequence encoding a protein of the invention, under the control of known regulatory sequences. The transformed host cells are cultured and the proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). As described above, expression of protein in mammalian cells requires an appropriate propeptide to assure secretion of the protein. The selection of suitable mammalian host cells and methods for transformation, culture, amplification, screening, product production and purification are known in the art. See, e.g., Gething and Sambrook, *Nature*, 293:620–625 (1981), or alternatively, Kaufman et al, *Mol. Cell. Biol.*, 5(7): 1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method. For expression of the protein in bacterial cells, DNA encoding a propeptide is not necessary.

Bacterial expression of mammalian proteins, including members of the TGF-β family is known to produce the proteins in a non-glycosylated form, and in the form of insoluble pellets, known as inclusion bodies. Techniques have been described in the art for solubilizing these inclusion bodies, denaturing the protein using a chaotropic agent, and refolding the protein sufficiently correctly to allow for their production in a soluble form. For example, see EP 0433225, the disclosure of which is hereby incorporated by reference.

Alternatively, methods have been devised which circumvent inclusion body formation, such as expression of gene fusion proteins, wherein the desired protein is expressed as a fusion protein with a fusion partner. The fusion protein is later subjected to cleavage to produce the desired protein. One example of such a gene fusion expression system for *E. coli* is based on use of the *E. coli* thioredoxin gene as a fusion partner, LaVallie et al., *Bio/Technology*, 11:187–193 (1993), the disclosure of which is hereby incorporated by reference.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these tendon/ligament-like tissue inducing proteins. Preferably the vectors contain the full novel DNA sequences described above which encode the novel factors of the invention. Additionally, the vectors contain appropriate expression control sequences permitting expression of the protein sequences. Alternatively, vectors incorporating modified sequences as described above are also embodiments of the present invention. Additionally, the sequence of SEQ ID NO:1 or SEQ ID NO:3 or SEQ ID NO:25 could be manipulated to express a mature protein by deleting propeptide sequences and replacing them with sequences encoding the complete propeptides of BMP proteins or members of the TGF-β superfamily. Thus, the present invention includes chimeric DNA molecules encoding a propeptide from a member of the TGF-β superfamily linked in correct reading frame to a DNA sequence encoding a protein having the amino acid sequence of SEQ ID NO:2 or SEQ ID NO:4 or SEQ ID NO:26, The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the invention may also be useful in the treatment of tendinitis, carpal tunnel syndrome and other tendon or ligament defects. The compositions of the present invention can also be used in other indications wherein it is desirable to heal or regenerate tendon and/or ligament tissue. Such indications include, without limitation, regeneration or repair of injuries to the periodontal ligament, such as occurs in tendonitis, and regeneration or repair of the tendon-to-bone attachment. The compositions of the present invention may provide an environment to attract tendon- or ligament-forming cells, stimulate growth of tendon- or ligament-forming cells or induce differentiation of progenitors of tendon- or ligament-forming cells.

The BMP-12 related proteins may be recovered from the culture medium and purified by isolating them from other proteinaceous materials from which they are co-produced and from other contaminants present. The proteins of the present invention are capable of inducing the formation of tendon/ligament-like tissue. These proteins may be further characterized by the ability to demonstrate tendon/ligament-like tissue formation activity in the rat ectopic implant assay described below. It is contemplated that these proteins may have ability to induce the formation of other types of tissue, such as ligaments, as well.

The tendontligament-like tissue inducing proteins provided herein also include factors encoded by the sequences similar to those of SEQ ID NO:1 or SEQ ID NO:25, but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO:2. These sequences, by virtue of sharing primary, secondary, or tertiary structural and conformational characteristics with tendon/ligament-like tissue growth factor polypeptides of SEQ ID NO:2 may possess tendon/ligament-like or other tissue growth factor biological properties in common therewith. Thus, they may be employed as biologically active substitutes for naturally-occurring tendon/ligament-like tissue inducing polypeptides in therapeutic compositions and processes.

Other specific mutations of the sequences of tendon/ligament-like tissue inducing proteins described herein involve modifications of glycosylation sites. These modifications may involve O-linked or N-linked glycosylation sites. For instance, the absence of glycosylation or only partial glycosylation results, from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences may be asparagine-X-threonine, asparagine-X-serine or asparagine-X-cysteine, where X is usually any amino acid except proline. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of protein will also result in production of a non-glycosylated protein, even if the glycosylation sites are left unmodified The compositions of the present invention comprise a purified BMP-12 related protein which may be produced by culturing a cell transformed with the DNA sequence of SEQ ID NO:1 or SEQ ID NO:25 and recovering and purifying protein having the amino acid sequence of SEQ ID NO:2 or SEQ ID NO:26 from the culture medium. The purified expressed protein is substantially free from other proteinaceous materials with which it is co-produced, as well as from other contaminants. The recovered purified protein is contemplated to exhibit tendon/ligament-like tissue formation activity, and other tissue growth activity, such as ligament regeneration. The proteins of the invention may be further characterized by the ability to demonstrate tendon/ligament-like tissue formation activity in the rat assay described below.

The compositions for inducing tendon/ligament-like tissue formation of the present invention may comprise an effective amount of a tendon/ligament-like tissue inducing protein, wherein said protein comprises the amino acid sequence of SEQ ID NO:2, preferably amino acids #–25, #1 or #3 to #103 or #104 of SEQ ID NO:2; or amino acids #1 or #19 to #120 of SEQ ID NO:26; as well as mutants and/or variants of SEQ ID NO:2 or SEQ ID NO:26, which exhibit the ability to form tendon and/or ligament like tissue.

Compositions of the present invention may further comprise additional proteins, such as additional members of the TGF-β superfamily of proteins, such as activins. Another aspect of the invention provides pharmaceutical compositions containing a therapeutically effective amount of a tendon/ligament-inducing protein, such as BMP-12 or VL-1, in a pharmaceutically acceptable vehicle or carrier. These compositions may be used to induce the formation of tendon/ligament-like tissue or other tissue. It is contemplated that such compositions may also be used for tendon and ligament repair, wound healing and other tissue repair, such as skin repair. It is further contemplated that proteins of the invention may increase neuronal survival and therefore be useful in transplantation and treatment of conditions exhibiting a decrease in neuronal survival. Compositions of the invention may further include at least one other therapeutically useful agent, such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/1 8098; BMP-9, disclosed in POT publication WO93/00432; and BMP-10 or BMP-11, disclosed in co-pending patent applications, Ser. No. 08/061,695, filed on May 12, 1993, now abandoned, a continuation-in-part of which has issued as U.S. Pat. No. 5,637,480, and Ser. No. 08/061,464, filed on May 12, 1993, now abandoned, a continuation-in-part of which has issued as U.S. Pat. No. 5,639,638. The disclosure of the above documents are hereby incorporated by reference herein.

The compositions of the invention may comprise, in addition to a tendon/ligament-inducing protein such as BMP-12 or VL-1 (BMP-13), other therapeutically useful agents including MP52, epidermal growth factor (EGF), fibroblast growth factor (FGF), platelet derived growth factor (PDGF), transforming growth factors (TGF-α and TGF-β), and fibroblast growth factor-4 (FGF-4), parathyroid hormone (PTH), leukemia inhibitory factor (LIF/HILDA/ DIA), insulin-like growth factors (IGF-I and IGF-II). Portions of these agents may also be used in compositions of the present invention. For example, a composition comprising both BMP-2 and BMP-12 implanted together gives rise to both bone and tendon/ligament-like tissue. Such a composition may be useful for treating defects of the embryonic joint where tendon, ligaments, and bone form simultaneously at contiguous anatomical locations, and may be useful for regenerating tissue at the site of tendon attachment to bone. It is contemplated that the compositions of the invention may also be used in wound healing, such as skin healing and related tissue repair. The types of wounds include, but are not limited to burns, incisions and ulcers. (See, e.g. PCT Publication WO84/01106 for discussion of wound healing and related tissue repair).

It is expected that the proteins of the invention may act in concert with or perhaps synergistically with other related proteins and growth factors. Further therapeutic methods and compositions of the invention therefore comprise a therapeutic amount of at least one protein of the invention with a therapeutic amount of at least one of the BMP proteins described above. Such compositions may comprise separate molecules of the BMP proteins or heteromolecules comprised of different BMP moieties. For example, a method and composition of the invention may comprise a disulfide linked dimer comprising a BMP-12 related protein subunit and a subunit from one of the "BMP" proteins described above. Thus, the present invention includes compositions comprising a purified BMP-12 related polypeptide which is a heterodimer wherein one subunit comprises the amino acid sequence from amino acid #1 to amino acid #104 of SEQ ID NO:2, and one subunit comprises an amino acid sequence for a bone morphogenetic protein selected from the group consisting of BMP-1, BMP-2, BMP-3, BMP4, BMP-5, BMP-6, BMP-7, BMP-8, BMP-9, BMP-10 and BMP-11. A further embodiment may comprise a heterodimer of disulfide bonded tendon/ligament-like tissue inducing moieties such as BMP-12, VL-1 (BMP-13) or MP52. For example the heterodimer may comprise one subunit comprising an amino acid sequence from #1 to #104 of SEQ ID NO:2 and the other subunit may comprise an amino acid sequence from #1 to #120 of SEQ ID NO:4 or #1 to #120 of SEQ ID NO:26. Further, compositions of the present invention may be combined with other agents beneficial to the treatment of the defect, wound, or tissue in question.

The preparation and formulation of such physiologically acceptable protein compositions, having due regard to pH, isotonicity, stability and the like, is within the skill of the art. The therapeutic compositions are also presently valuable for veterinary applications due to the lack of species specificity in TGF-β proteins. Particularly domestic animals and thoroughbred horses in addition to humans are desired patients for such treatment with the compositions of the present invention.

The therapeutic method includes administering the composition topically, systemically, or locally as an injectable and/or implant or device. When administered, the therapeutic composition for use in this invention is, of course, in a pyrogen-free, physiologically acceptable form. Further, the composition may desirably be encapsulated or injected in a viscous form for delivery to the site of tissue damage. Topical administration may be suitable for wound healing and tissue repair. Therapeutically useful agents other than the proteins which may also optionally be included in the composition as described above, may alternatively or additionally, be administered simultaneously or sequentially with the composition in the methods of the invention. In addition, the compositions of the present invention may be used in conjunction with presently available treatments for tendon/ligament injuries, such as suture (e.g., vicryl sutures or surgical gut sutures, Ethicon Inc., Somerville, N.J.) or tendon/ligament allograft or autograft, in order to enhance or accelerate the healing potential of the suture or graft. For example, the suture, allograft or autograft may be soaked in the compositions of the present invention prior to implantation. It may also be possible to incorporate the protein or composition of the invention onto suture materials, for example, by freeze-drying.

The compositions may include an appropriate matrix and/or sequestering agent as a carrier. For instance, the matrix may support the composition or provide a surface for tendon/ligament-like tissue formation and/or other tissue formation. The matrix may provide slow release of the protein and/or the appropriate environment for presentation thereof. The sequestering agent may be a substance which aids in ease of administration through injection or other means, or may slow the migration of protein from the site of application.

The choice of a carrier material is based on biocompatibility, biodegradability, mechanical properties, cosmetic appearance and interface properties. The particular application of the compositions will define the appropriate formulation. Potential matrices for the compositions may be biodegradable and chemically defined. Further matrices are comprised of pure proteins or extracellular matrix components. Other potential matrices are nonbiodegradable and chemically defined. Preferred matrices include collagen-based materials, including sponges, such as Helistat® (Integra LifeSciences, Plainsboro, N.J.), or collagen in an injectable form, as well as sequestering agents, which may be biodegradable, for example hyalouronic acid derived. Biodegradable materials, such as cellulose films, or surgical meshes, may also serve as matrices. Such materials could be sutured into an injury site, or wrapped around the tendon/ligament.

Another preferred class of carrier are polymeric matrices, including polymers of poly(lactic acid), poly(glycolic acid) and copolymers of lactic acid and glycolic acid. These matrices may be in the form of a sponge, or in the form of porous particles, and may also include a sequestering agent. Suitable polymer matrices are described, for example, in WO93/00050, the disclosure of which is incorporated herein by reference.

Preferred families of sequestering agents include blood, fibrin clot and/or cellulosic materials such as alkylcelluloses (including hydroxyalkylcelluloses) including methylcellulose, ethylcellulose, hydroxyethylcellulose. hydroxypropylcellulose, hydroxypropyl-methylcellulose, and carboxymethylcellulose. the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the activity of the progenitor cells.

Additional optional components useful in the practice of the subject application include, e.g. cryogenic protectors such as mannitol, sucrose, lactose, glucose, or glycine (to protect the protein from degradation during lyophilization), antimicrobial preservatives such as methyl and propyl parabens and benzyl alcohol; antioxidants such as EDTA, citrate and BHT (butylated hydroxytoluene); and surfactants such as poly(sorbates) and poly(oxyethylenes); etc.

As described above, the compositions of the invention may be employed in methods for treating a number of tendon defects, such as the regeneration of tendon/ligament-like tissue in areas of tendon or ligament damage, to assist in repair of tears of tendon tissue, ligaments, and various other types of tissue defects or wounds. These methods, according to the invention, entail administering to a patient needing such tendon/ligament-like tissue or other tissue repair, a composition comprising an effective amount of a tendon/ligament-like tissue inducing protein, such as described in SEQ ID NO:2, SEQ ID NO:4 and/or SEQ ID NO:26. These methods may also entail the administration of a tendon/ligament-like tissue inducing protein in conjunction with at least one of the BMP proteins described above.

In another embodiment, the methods may entail administration of a heterodimeric protein in which one of the monomers is a tendon/ligament-like tissue inducing polypeptide, such as BMP-12, VL-1 (BMP-13) or MP52, and the second monomer is a member of the TGF-β superfamily of growth factors. In addition, these methods may also include the administration of a tendon/ligament-like tissue inducing protein with other growth factors including EGF, FGF, TGF-α, TGF-β, and IGF.

Thus, a further aspect of the invention is a therapeutic method and composition for repairing tendon/ligament-like tissue, for repairing tendon or ligament as well as treating tendinitis and other conditions related to tendon or ligament defects. Such compositions comprise a therapeutically effective amount of one or more tendon/ligament-like tissue inducing proteins, such as BMP-12, a BMP-12 related protein, or MP52, in admixture with a pharmaceutically acceptable vehicle, carrier or matrix.

The dosage regimen will be determined by the attending physician considering various factors which modify the action of the composition, e.g., amount of tendon or ligament tissue desired to be formed, the site of tendon or ligament damage, the condition of the damaged tendon or ligament, the size of a wound, type of damaged tissue, the patient's age, sex, and diet, the severity of any infection, time of administration and other clinical factors. The dosage may vary with the type of matrix used in the reconstitution and the types of additional proteins in the composition. The addition of other known growth factors, such as IGF-I (insulin like growth factor I), to the final composition, may also affect the dosage.

Progress can be monitored by periodic assessment of tendon/ligament-like tissue formation, or tendon or ligament growth and/or repair. The progress can be monitored by methods known in the art, for example, X-rays, arthroscopy, histomorphometric determinations and tetracycline labeling.

The following examples illustrate practice of the present invention in recovering and characterizing human tendon/ligament-like tissue inducing protein and employing them to recover the other tendon/ligament-like tissue inducing proteins, obtaining the human proteins, expressing the proteins via recombinant techniques, and demonstration of the ability of the compositions of the present invention to form tendon/ligament-like tissue in an in vivo model. Although the examples demonstrate the invention with respect to BMP-12, with minor modifications within the skill of the art, the same results are believed to be attainable with MP52 and VL-1.

EXAMPLE 1

Isolation of DNA

DNA sequences encoding BMP-12 and BMP-12 related proteins may be isolated by various techniques known to those skilled in the art. As described below, oligonucleotide primers may be designed on the basis of amino acid sequences present in other BMP proteins, Vg-1 related proteins and other proteins of the TGF-β superfamily. Regions containing amino acid sequences which are highly conserved within the BMP family of proteins and within other members of the TGF-β superfamily of proteins can be identified and consensus amino acid sequences of these highly conserved regions can be constructed based on the similarity of the corresponding regions of individual BMP/TGF-β/Vg-1 proteins. An example of such a consensus amino acid sequence is indicated below.

Consensus Amino Acid Sequence (1)

Trp-Gln/Asn-Asp-Trp-Ile-Val/Ile-Ala (SEQ ID NO:16)

Where X/Y indicates that either amino acid residue may appear at that position.

The following oligonucleotide is designed on the basis of the above identified consensus amino acid sequence (1):

1: <u>CGGATCC</u>TGGVANGAYTGGATHRTNGC (SEQ ID NO:17)

This oligonucleotide sequence is synthesized on an automated DNA synthesizer. The standard nucleotide symbols in the above identified oligonucleotide primer are as follows: A,adenosine; C,cytosine; G,guanine; T,thymine; N,adenosine or cytosine or guanine or thymine; R,adenosine or cytosine; Y,cytosine or thymine; H,adenosine or cytosine or thymine; V,adenosine or cytosine or guanine; D,adenosine or guanine or thymine.

The first seven nucleotides of oligonucleotide #1 (underlined) contain the recognition sequence for the restriction endonuclease BamHI in order to facilitate the manipulation of a specifically amplified DNA sequence encoding the BMP-12 protein and are thus not derived from the consensus amino acid sequence (1) presented above.

A second consensus amino acid sequence is derived from another highly conserved region of BMP/TGF-β/Vg-1 proteins as described below:

His-Ala-Ile-Val/Leu-Gln-Thr (SEQ ID NO:18)

The following oligonucleotide is designed on the basis of the above identified consensus amino acid sequence (2):

2: <u>TTTCTAGA</u>ARNGTYTGNACDATNGCRTG (SEQ ID NO:19)

This oligonucleotide sequence is synthesized on an automated DNA synthesizer. The same nucleotide symbols are used as described above.

The first seven nucleotides of oligonucleotide #1 (underlined) contain the recognition sequence for the restriction endonuclease XbaI in order to facilitate the manipulation of a specifically amplified DNA sequence encoding the BMP-12 protein and are thus not derived from the consensus amino acid sequence (2) presented above.

It is contemplated that the BMP-12 protein of the invention and other BMP/TGF-β/Vg-1 related proteins may contain amino acid sequences similar to the consensus amino acid sequences described above and that the location of those sequences within a BMP-12 protein or other novel related proteins would correspond to the relative locations in the proteins from which they were derived. It is further contemplated that this positional information derived from the structure of other BMP/TGF-β/Vg-1 proteins and the oligonucleotide sequences #1 and #2 which have been derived from consensus amino acid sequences (1) and (2), respectively, could be utilized to specifically amplify DNA sequences encoding the corresponding amino acids of a BMP-12 protein or other BMP/TGF-β/Vg-1 related proteins.

Based on the knowledge of the gene structures of BMP/TGF-β/Vg-1 proteins it is further contemplated that human genomic DNA can be used as a template to perform specific amplification reactions which would result in the identification of BMP-12 BMP/TGF-β/Vg-1 (BMP-12 related protein) encoding sequences. Such specific amplification reactions of a human genomic DNA template could be initiated with the use of oligonucleotide primers #1 and #2 described earlier. Oligonucleotides #1 and #2 identified above are utilized as primers to allow the specific amplification of a specific nucleotide sequence from human genomic DNA. The amplification reaction is performed as follows:

Human genomic DNA (source: peripheral blood lymphocytes), provided by Ken Jacobs of Genetics Institute, is sheared by repeated passage through a 25 gauge needle, denatured at 100° C. for 5 minutes and then chilled on ice before adding to a reaction mixture containing 200 μM each deoxynucleotide triphosphates (dATP, dGTP, dCTP and dTTP), 10 mM Tris-HCl pH 8.3, 50 mM KCl, 1.5 mM MgCl$_2$, 0.001% gelatin, 1.25 units Taq DNA polymerase, 100 pM oligonucleotide #1 and 100 pM oligonucleotide #2. This reaction mixture is incubated at 94° C. for two minutes and then subjected to thermal cycling in the following manner: 1 minute at 94° C., 1 minute at 40° C., 1 minute at 72° C for three cycles; then 1 minute at 94° C., 1 minute at 55° C., 1 minute at 72° C. for thirty-seven cycles, followed by a 10 minute incubation at 72° C.

The DNA which is specifically amplified by this reaction is ethanol precipitated, digested with the restriction endonucleases BamHI and XbaI and subjected to agarose gel electrophoresis. A region of the gel, corresponding to the predicted size of the BMP-12 or other BMP/TGF-β/Vg-1 encoding DNA fragment, is excised and the specifically amplified DNA fragments contained therein are electroeluted and subcloned into the plasmid vector pGEM-3 between the XbaI and BamHI sites of the polylinker. DNA sequence analysis of one of the resulting BMP-12 related subclones indicates the specifically amplified DNA sequence product contained therein encodes a portion of the BMP-12 protein of the invention.

The DNA sequence (SEQ ID NO:5) and derived amino acid sequence (SEQ ID NO:6) of this specifically amplified DNA fragment of BMP-12 are shown in the SEQUENCE Listings.

Nucleotides #1–#26 of SEQ ID NO:5 comprise a portion of oligonucleotide #1 and nucleotides #103–#128 comprise a portion of the reverse compliment of oligonucleotide #2 utilized to perform the specific amplification reaction. Due to the function of oligonucleotides #1 and #2 in initiating the amplification reaction, they may not correspond exactly to the actual sequence encoding a BMP-12 protein and are therefore not translated in the corresponding amino acid derivation (SEQ ID NO:6).

DNA sequence analysis of another subclone indicates that the specifically amplified DNA product contained therein encodes a portion of another BMP/TGF-β/Vg-1 (BMP-12 related) protein of the invention named VL-1.

The DNA sequence (SEQ ID NO:7) and derived amino acid sequence (SEQ ID NO:8) of this specifically amplified DNA fragment are shown in the Sequence Listings.

Nucleotides #1–#26 of SEQ ID NO:7 comprise a portion of oligonucleotide #1 and nucleotides #103–#128 comprise a portion of the reverse compliment of oligonucleotide #2 utilized to perform the specific amplification reaction. Due to the function of oligonucleotides #1 and #2 in initiating the amplification reaction, they may not correspond exactly to the actual sequence encoding a VL-1 protein of the invention and are therefore not translated in the corresponding amino acid derivation (SEQ ID NO:8).

The following oligonucleotide probe is designed on the basis of the specifically amplified BMP-12 human DNA sequence set forth above (SEQ ID NO:5) and synthesized on an automated DNA synthesizer:

3: CCACTGCGAGGGCCTTTGCGACTTC-CCTTTGCGTTCGCAC (SEQ ID NO:20)

This oligonucleotide probe is radioactively labeled with $^{32}$P and employed to screen a human genomic library constructed in the vector λFIX (Stratagene catalog #944201). 500,000 recombinants of the human genomic library are plated at a density of approximately 10,000 recombinants per plate on 50 plates. Duplicate nitrocellulose replicas of the recombinant bacteriophage plaques and hybridized to oligonucleotide probe #3 in standard hybridization buffer (SHB=5×SSC, 0.1% SDS, 5×Denhardt's, 100 μg/ml salmon sperm DNA) at 65° C. overnight. The following day the radioactively labelled oligonucleotide containing hybridization solution is removed an the filters are washed with 0.2×SSC, 0.1% SDS at 65° C. A single positively hybridizing recombinant is identified and plaque purified. This plaque purified recombinant bacteriophage clone which hybridizes to the BMP-12 oligonucleotide probe #3 is designated λHuG-48. A bacteriophage plate stock is made and bacteriophage DNA is isolated from the λHuG-48 human genomic clone. The bacteriophage λHuG-48 has been deposited with the American Type Culture Collection, 12301 Parklawn Drive, Rockville, Md. "ATCC" under the accession #75625 on Dec. 7, 1993. This deposit meets the requirements of the Budapest Treaty of the International Recognition of the Deposit of Microorganisms for the Purpose of Patent Procedure and Regulations thereunder. The oligonucleotide hybridizing region of this recombinant, λHuG-48, is localized to a 3.2 kb BamHI fragment. This fragment is subcloned into a plasmid vector (pGEM-3) and DNA sequence analysis is performed. This plasmid subclone is designated PCR1-1#2 and has been deposited with the American Type Culture Collection, 12301 Parklawn Drive, Rockville, Md. "ATCC" under the accession #69517 on Dec. 7, 1993. This deposit meets the requirements of the Budapest Treaty of the International Recognition of the Deposit of Microorganisms for the Purpose of Patent Procedure and Regulations thereunder. The partial DNA sequence (SEQ ID NO:1) and derived amino acid sequence (SEQ ID NO:2) of the 3.2 kb DNA insert of the plasmid subclone PCR1-1#2, derived from clone λHuG-48, are shown in the Sequence Listings.

It should be noted that nucleotides #639-#714 of SEQ ID NO:1 correspond to nucleotides #27-#102 of the specifically amplified BMP-12 encoding DNA fragment set forth in SEQ ID NO:5 thus confirming that the human genomic bacteriophage clone λHuG-48 and derivative subclone PCR1-1#2 encode at least a portion of the BMP-12 protein of the invention. The nucleotide sequence of a portion of the 3.2 kb BamHI insert of the plasmid PCR1-1#2 contains an open reading frame of at least 882 base pairs, as defined by nucleotides #1-#882 of SEQ ID NO:1. This open reading frame encodes at least 294 amino acids of the human BMP-12 protein of the invention. The encoded 294 amino acid human BMP-12 protein includes the full mature human BMP-12 protein (amino acids #1-#104 of SEQ ID NO:2), as well as the C-terminal portion of the propeptide region of the primary translation product (amino acid #-190 to #-1 of SEQ ID NO:2).

Additional DNA sequence of the 3.2 kb BamHI insert of the plasmid PCR1-1#2 set forth in SEQ ID NO:33 demonstrates the presence of an 1164 bp open reading frame, as defined by nucleotides #138 through #1301 of SEQ ID NO:33. [NOTE that all the sequence disclosed in SEQ ID NO:1 is contained within SEQ ID NO:33]. As this sequence is derived from a genomic clone it is difficult to determine the boundary between the 5' extent of coding sequence and the 3' limit of intervening sequence (intron/non-coding sequence).

Based on the knowledge of other BMP proteins and other proteins within the TGF-β family, it is predicted that the precursor polypeptide would be cleaved at the multibasic sequence Arg-Arg-Gly-Arg (SEQ ID NO:2, residues -4 to -1) in agreement with a proposed consensus proteolytic processing sequence of Arg-X-X-Arg (SEQ ID NO:2, residues -4 to -1). Cleavage of the BMP-12 precursor polypeptide is expected to generate a 104 amino acid mature peptide beginning with the amino acid Ser at position #1 of SEQ ID NO:2. The processing of BMP-12 into the mature form is expected to involve dimerization and removal of the N-terminal region in a manner analogous to the processing of the related protein TGF-β [Gentry et al., Molec & Cell. Biol., 8:4162 (1988); Derynck et al. Nature, 316:701 (1985)].

It is contemplated therefore that the mature active species of BMP-12 comprises a homodimer of two polypeptide subunits, each subunit comprising amino acids #1 to #104 of SEQ ID NO:2 with a predicted molecular weight of approximately 12,000 daltons. Further active species are contemplated comprising at least amino acids #3 to #103 of SEQ ID NO:2, thereby including the first and last conserved cysteine residue. As with other members of the TGF-β/BMP family of proteins, the carboxy-terminal portion of the BMP-12 protein exhibits greater sequence conservation than the more amino-terminal portion. The percent amino acid identity of the human BMP-12 protein in the cysteine-rich C-terminal domain (amino acids #3-#104) to the corresponding region of human BMP proteins and other proteins within the TGF-β family is as follows: BMP-2, 55%; BMP-3, 43%; BMP-4, 53%; BMP-5, 49%; BMP-6, 49%; BMP-7, 50%; BMP-8, 57%; BMP-9, 48%; BMP-10, 57%; activin WC (BMP-11), 38%; Vg1, 46%; GDF-1, 47%; TGF-β1, 36%; TGF-β2, 36%; TGF-β3, 39%; inhibin β(B), 36%; inhibin β(A), 41%.

The human BMP-12 DNA sequence (SEQ ID NO:1), or a portion thereof, can be used as a probe to identify a human cell line or tissue which synthesizes BMP-12 mRNA. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from the coding sequence of human BMP-12.

Alternatively, the human BMP-12 sequence is used to design oligonucleotide primers which will specifically amplify a portion of the BMP-12 encoding sequence located in the region between the primers utilized to perform the specific amplification reaction. It is contemplated that these human BMP-12 derived primers would allow one to specifically amplify corresponding BMP-12 encoding sequences from mRNA, cDNA or genomic DNA templates. Once a positive source has been identified by one of the above described methods, mRNA is selected by oligo (dT) cellulose chromatography and cDNA is synthesized and cloned in λgt10 or other λ bacteriophage vectors known to those skilled in the art, for example, λZAP by established techniques (Toole et al., supra). It is also possible to perform the oligonucleotide primer directed amplification reaction, described above, directly on a pre-established human cDNA or genomic library which has been cloned into a λ bacteriophage vector. In such cases, a library which yields a specifically amplified DNA product encoding a portion of the human BMP-12 protein could be screened directly, utilizing the fragment of amplified BMP-12 encoding DNA as a probe.

Oligonucleotide primers designed on the basis of the DNA sequence of the human BMP-12 genomic clone λHuG-48 are predicted to allow the specific amplification of human BMP-12 encoding DNA sequences from pre-established human cDNA libraries which are commercially available (ie. Stratagene, La Jolla, Calif. or Clontech Laboratories, Inc., Palo Alto, Calif.). The following oligonucleotide primer is designed on the basis of nucleotides #571 to #590 of the DNA sequence set forth in SEQ ID NO:1 and synthesized on an automated DNA synthesizer:

4: TGCGGATCCAGCCGCTGCAGCCGCAAGCC (SEQ ID NO:21)

The first nine nucleotides of primer #4 (underlined) comprise the recognition sequence for the restriction endonuclease BamHI which can be used to facilitate the manipulation of a specifically amplified DNA sequence encoding the human BMP-12 protein of the invention and are thus not derived from the DNA sequence presented in SEQ ID NO:1.

The following oligonucleotide primer is designed on the basis of nucleotides #866–#885 of the DNA sequence set forth in SEQ ID NO:1 and synthesized on an automated DNA synthesizer:

5 GACTCTAGACTACCTGCAGCCGCAGGCCT (SEQ ID NO:22)

The first nine nucleotides of primer #5 (underlined) comprise the recognition sequence for the restriction endonuclease XbaI which can be used to facilitate the manipulation of a specifically amplified DNA sequence encoding the human BMP-12 protein of the invention and are thus not derived from the DNA sequence presented in SEQ ID NO:1.

The standard nucleotide symbols in the above identified primers are as follows: A, adenine; C, cytosine; G, guanine; T, thymine.

Primers #4 and #5 identified above are utilized as primers to allow the amplification of a specific BMP-12 encoding nucleotide sequence from pre-established cDNA libraries which may include the following: human fetal brain cDNA/ λZAPII (Stratagene catalog #936206), human liver/λUNI-ZAP XR (Stratagene Catalog #937200), human lung/λUNI-ZAP XR (Stratagene catalog #937206), and human fetal spleen/UNI-ZAP XR (Stratagene catalog #937205).

Approximately 1×10$^8$ pfu (plaque forming units) of λbacteriophage libraries containing human cDNA inserts such as those detailed above are denatured at 95° C. for five minutes prior to addition to a reaction mixture containing 200 μM each deoxynucleotide triphosphates (dATP, dGTP, dCTP and dTTP) 10 mM Tris-HCl pH 8.3, 50 mM KCl, 1.5 mM MgCl$_2$, 0.001% gelatin, 1.25 units Taq DNA polymerase, 100 pM oligonucleotide primer #4 and 100 pM oligonucleotide primer #5. The reaction mixture is then subjected to thermal cycling in the following manner: 1 minute at 94° C., 1 minute at 50° C., 1 minute at 72° C. for thirty-nine cycles followed by 10 minutes at 72° C.

The DNA which is specifically amplified by this reaction would be expected to generate a BMP-12 encoding product of approximately 333 base pairs, the internal 315 bp of which correspond to nucleotides #571 to #885 of SEQ ID NO:1 and also including 9 bp at each end of the BMP-12 specific fragment which correspond to the restriction sites defined by nucleotides #1–#9 of primers #4 and #5. The resulting 333 bp DNA product is digested with the restriction endonucleases BamHI and XbaI, phenol extracted, chloroform extracted and ethanol precipitated.

Alternatively, to ethanol precipitation, buffer exchange and removal of small fragments of DNA resulting from the BamHI/XbaI restriction digest is accomplished by dilution of the digested DNA product in 10 mM Tris-HCl pH 8.0, 1 mM EDTA followed by centrifugation through a Centricon™ 30 microconcentrator (W. R. Grace & Co., Beverly, Mass.; Product #4209). The resulting BamHI/XbaI digested amplified DNA product is subcloned into a plasmid vector (ie. pBluescript, pGEM-3 etc.) between the BamHI and XbaI sites of the polylinker region. DNA sequence analysis of the resulting subclones would be required to confirm the integrity of the BMP-12 encoding insert. Once a positive cDNA source has been identified in this manner, the corresponding cDNA library from which a 333 bp BMP-12 specific sequence was amplified could be screened directly with the 333 bp insert or other BMP-12 specific probes in order to identify and isolate cDNA clones encoding the full-length BMP-12 protein of the invention.

Additional methods known to those skilled in the art may be used to isolate other full-length cDNAs encoding human BMP-12 related proteins, or full length cDNA clones encoding BMP-12 related proteins of the invention from species other than humans, particularly other mammalian species.

The following examples demonstrate the use of the human BMP-12 sequence to isolate homologues from BMP-12 related proteins in a murine genomic DNA library.

The DNA sequence which encodes the human BMP-12 protein of the invention is predicted to be significantly homologous to BMP-12 and BMP-12 related sequences from species other than humans that it could be utilized to specifically amplify DNA sequences from those other species which would encode the corresponding BMP-12 related proteins. Specifically, the following oligonucleotides are designed on the basis of the human BMP-12 sequence (SEQ ID NO:1) and are synthesized on an automated DNA synthesizer:

6: GCGGATCCAAGGAGCTCGGCTGGGACGA (SEQ ID NO:23)

7: GGAATTCCCCACCACCATGTCCTCGTAT (SEQ ID NO:24)

The first eight nucleotides of oligonucleotide primers #6 and #7 (underlined) comprise the recognition sequence for the restriction endonucleases BamHI and EcoRI, respectively. These sequences are utilized to facilitate the manipulation of a specifically amplified DNA sequence encoding a BMP-12 or BMP-12 related protein from a species other than human and are thus not derived from the DNA sequence presented in SEQ ID NO:1. Oligonucleotide primer #6 is designed on the basis of nucleotides #607–#626 of SEQ ID NO:1 Oligonucleotide primer #7 is designed on the basis of the reverse compliment of nucleotides #846–#865 of the DNA sequence set forth in SEQ ID NO:1.

Oligonucleotide primers #6 and #7 identified above are utilized as primers to allow the amplification of specific BMP-12 related sequences from genomic DNA derived from species other than humans. The amplification reaction is performed as follows:

Murine genomic DNA (source: strain Balb c) is sheared by repeated passage through a 25 gauge needle, denatured at 100° C. for five minutes and then chilled on ice before adding to a reaction mixture containing 200 μM each deoxynucleotide triphosphates (dATP, DGTP, dCTP and dTTP) 10 mM Tris-HCl pH 8.3, 50 mM KCl, 1.5 mM MgCl$_2$, 0.001% gelatin, 1.25 units Taq DNA polymerase, 100 pM oligonucleotide primer #6 and 100 pM oligonucleotide primer #7. The reaction mixture is then subjected to thermal cycling in the following manner: 1 minute at 95° C., 1 minute at 55° C., 1 minute at 72° C. for forty cycles followed by 10 minutes at 72° C.

The DNA which is specifically amplified by this reaction is ethanol precipitated, digested with the restriction endonucleases BamHI and EcoRI and subjected to agarose gel electrophoresis. A region of the gel, corresponding to the predicted size of the murine BMP-12 or BMP-12 related encoding DNA fragment, is excised and the specifically amplified DNA fragments contained therein are extracted (by electroelution or by other methods known to those skilled in the art) and subcloned in to a plasmid vector, such as pGEM-3 or pBluescript between the BamHI and EcoRI sites of the polylinker. DNA sequence analysis of one of the resulting subclones named mV1, indicates that the specifically amplified DNA sequence contained therein encodes a portion of a protein which appears to be the murine homolog to either the BMP-12 or VL-1 sequence of the invention. The DNA sequence (SEQ ID NO:10) and derived amino acid sequence (SEQ ID NO:1) of this specifically amplified murine DNA fragment are shown in the sequence listings.

Nucleotides #1–#26 of SEQ ID NO:10 comprise a portion of oligonucleotide #6 and nucleotides #246–#272 comprise a portion of the reverse compliment of oligonucleotide #7 utilized to perform the specific amplification reaction. Nucleotide #27 of SEQ ID NO:10 appears to be the last nucleotide of a codon triplet, and nucleotides #244–#245 of SEQ ID NO:10 appear to be the first two nucleotides of a codon triplet. Therefore, nucleotides #28 to #243 of SEQ ID NO:10 correspond to a partial coding sequence of mV1. Due to the function of oligonucleotides #6 and #7 in initiating the amplification reaction, they may not correspond exactly to the actual sequence encoding the murine homolog to the human BMP-12 or VL-1 protein of the invention and are therefore not translated in the corresponding amino acid sequence derivation (SEQ ID NO:11).

Oligonucleotide probes designed on the basis of the specifically amplified murine BMP-12 or VL-1 DNA sequence set forth in SEQ ID NO:10 can be utilized by those skilled in the art to identify full-length murine BMP-12 or VL-1 encoding clones (either cDNA or genomic).

DNA sequence analysis of another of the resulting subclones named mV2, indicates that the specifically amplified DNA sequence contained therein encodes a portion of a murine BMP-12 related sequence of the invention. The DNA sequence (SEQ ID NO:12) and derived amino acid sequence (SEQ ID NO:13) of this specifically amplified murine DNA fragment are shown in the sequence listings.

Nucleotides #1–#26 of SEQ ID NO:12 comprise a portion of oligonucleotide #6 and nucleotides #246–#272 comprise a portion of the reverse compliment of oligonucleotide #7 utilized to perform the specific amplification reaction. Nucleotide #27 of SEQ ID NO:12 appears to be the last nucleotide of a codon triplet, and nucleotides #244–#245 of SEQ ID NO:12 appear to be the first two nucleotides of a codon triplet. Therefore, nucleotides #28 to #243 of SEQ ID NO:12 correspond to a partial coding sequence of mV2. Due to the function of oligonucleotides #6 and #7 in initiating the amplification reaction, they may not correspond exactly to the actual sequence encoding the murine BMP-12 related protein of the invention and are therefore not translated in the corresponding amino acid sequence derivation. (SEQ ID NO:13).

Oligonucleotide probes designed on the basis of the specifically amplified murine BMP-12 related DNA sequence set forth in SEQ ID NO:12 can be utilized by those skilled in the art to identify full-length murine BMP-12 related encoding clones (either cDNA or genomic).

DNA sequence analysis of another of the resulting subclones named mV9, indicates that the specifically amplified DNA sequence contained therein encodes a portion of a murine BMP-12 related sequence of the invention. This sequence appears to be the murine homolog to the human MP52 DNA sequence described at SEQ ID NO:3. The DNA sequence (SEQ ID NO:14) and derived amino acid sequence (SEQ ID NO:15) of this specifically amplified murine DNA fragment are shown in the sequence listings.

Nucleotides #1–#26 of SEQ ID NO:14 comprise a portion of oligonucleotide #6 and nucleotides #246–#272 comprise a portion of the reverse compliment of oligonucleotide #7 utilized to perform the specific amplification reaction. Nucleotide #27 of SEQ ID NO:14 appears to be the last nucleotide of a codon triplet, and nucleotides #244–#245 of SEQ ID NO:14 appear to be the first two nucleotides of a codon triplet. Therefore, nucleotides #28 to #243 of SEQ ID NO:14 correspond to a partial coding sequence of mV9. Due to the function of oligonucleotides #6 and #7 in initiating the amplification reaction, they may not correspond exactly to the actual sequence encoding the murine BMP-12 related protein of the invention and are therefore not translated in the corresponding amino acid sequence derivation (SEQ ID NO:15).

Oligonucleotide probes designed on the basis of the specifically amplified murine BMP-12 related DNA sequence set forth in SEQ ID NO:14 can be utilized by those skilled in the art to identify full-length murine BMP-12 related encoding clones (either cDNA or genomic).

Alternatively, oligonucleotide primers #6 and #7 identified above are utilized as primers to allow the specific amplification of a 275 base pair DNA probe, the internal 259 bp of which correspond to nucleotides #607 to #865 of SEQ ID NO:1, from the BMP-12 encoding plasmid subclone PCR1-1#2. This 275 bp DNA probe was radioactively labelled with $^{32}$P and employed to screen a murine genomic library constructed in the vector λ FIX II (Stratagene catalog #946306). 1 million recombinants of the murine genomic library are plated at a density of approximately 20,000 recombinants per plate on 50 plates. Duplicate nitrocellulose replicas of the recombinant bacteriophage plaques are hybridized, under reduced stringency conditions, to the specifically amplified 333 bp probe in standard hybridization buffer (SHB=5×SSC, 0.1% SDS, 5×Denhardt's, 100 μg/ml salmon sperm DNA) at 60° C. overnight. The following day the radioactively labelled oligonucleotide containing hybridization solution is removed an the filters are washed, under reduced stringency conditions, with 2×SSC, 0.1% SDS at 60° C. Multiple positively hybridizing recombinants are identified and plaque purified. Fragments of the positively hybridizing murine genomic recombinant clones are subcloned into standard plasmid vectors (i.e. pGEM-3) and subjected to DNA sequence analysis.

DNA sequence analysis of one of these subclones named MVR3 indicates that it encodes a portion of the mouse gene corresponding to the PCR product mV1 (murine homolog of the human BMP-12 sequence set forth in SEQ ID NO:1) described above. The partial DNA sequence of this subclone and corresponding amino acid translation are set forth in SEQ ID NO: 29 and SEQ ID NO:30 respectively.

DNA sequence analysis of another one of these subclones named MVR32 indicates that it encodes a portion of the mouse gene corresponding to the PCR product mV2 (murine homolog of the human VL-1 sequence set forth in SEQ ID NO:7) described above. The partial DNA sequence of this subclone and corresponding amino acid translation are set forth in SEQ ID NO: 31 and SEQ ID NO:32 respectively.

DNA sequence analysis of another of these subclones named MVR23 indicates that it encodes a portion of the mouse gene corresponding to the PCR product mV9 (murine homolog of the MP-52 sequence set forth in SEQ ID NO:3) described above.

In a similar manner to that which is described above for identifying and isolating human genomic clones encoding the BMP-12 protein of the invention, oligonucleotide probe (s) corresponding to the VL-1 encoding sequence set forth in SEQ ID NO:7 can be designed and utilized to identify human genomic or cDNA sequences encoding the VL-1 (BMP-13) protein. These oligonucleotides would be designed to regions specific for VL-1 encoding sequences and would therefore be likely to be derived from regions of the lowest degree of nucleotide sequence identity between the specifically amplified VL-1 encoding sequence (SEQ ID NO:7) and the specifically amplified BMP-12 encoding sequence (SEQ ID NO:5).

Alternatively, oligonucleotide primers #4 and #5 identified above are utilized as primers to allow the specific amplification of a 333 base pair DNA probe, the internal 315 bp of which correspond to nucleotides #571 to #885 of SEQ ID NO:1, from the BMP-12 encoding plasmid subclone PCR1-1#2. This 333 bp DNA probe was radioactively labelled with $^{32}$P and employed to screen a human genomic library constructed in the vector λDASH II (Stratagene catalog #945203). 1 million recombinants of the human genomic library are plated at a density of approximately 20,000 recombinants per plate on 50 plates. Duplicate nitrocellulose replicas of the recombinant bacteriophage plaques are hybridized, under reduced stringency conditions, to the specifically amplified 333 bp probe in standard hybridization buffer (SHB=5×SSC, 0.1% SDS, 5×Denhardt's, 100 μg/ml salmon sperm DNA) at 60° C. overnight. The following day the radioactively labelled oligonucleotide containing hybridization solution is removed an the filters are washed, under reduced stringency conditions, with 2×SSC, 0.1% SDS at 60° C. Multiple (approximately 15) positively hybridizing recombinants are identified and plaque purified.

In order to distinguish positively hybridizing recombinants encoding the VL-1 protein of the invention from BMP-12 and other BMP-12-related encoding recombinants which would be predicted to hybridize positively to the 333 bp DNA probe generated from the BMP-12 encoding plasmid PCR1-1#2 utilized in this screening procedure, the following oligonucleotide probe, based on the VL-1 sequence set forth in SEQ ID NO:7, is designed and synthesized on an automated DNA synthesizer:

8: TGTATGCGACTTCCCGC [SEQUENCE ID NO: 35]

An oligonucleotide corresponding to nucleotides #60 to #76 of SEQ ID NO:7 which contains 5 nucleotide differences to the corresponding region of the BMP-12 encoding sequence set forth in SEQ ID NO:1 (nucleotides #672 to #689) One of the recombinant bacteriophage clones which hybridizes to the VL-1 oligonucleotide probe #8 is designated λJLDc31. This recombinant bacteriophage clone is plaque purified, a bacteriophage plate stock is made and bacteriophage DNA is isolated from the λJLDc31 human genomic clone. The bacteriophage λJLDc31 has been deposited with the American Type Culture Collection, 12301 Parklawn Drive, Rockville, Md. "ATCC" under the accession #75922 on Oct. 20, 1994. This deposit meets the requirements of the Budapest Treaty of the International Recognition of the Deposit of Microorganisms for the Purpose of Patent Procedure and Regulations thereunder. The oligonucleotide hybridizing region of this recombinant, λJLDc31, is localized to a 2.5 kb Eco RI fragment. This fragment is subcloned into a plasmid vector (pGEM-3) and DNA sequence analysis is performed. This plasmid subclone is designated pGEMJLDc31/2.5 and has been deposited with the American Type Culture Collection, 12301 Parklawn Drive, Rockville, Md. "ATCC" under the accession #69710 on Oct. 20, 1994. This deposit meets the requirements of the Budapest Treaty of the International Recognition of the Deposit of Microorganisms for the Purpose of Patent Procedure and Regulations thereunder.

The partial DNA sequence (SEQ ID NO:25) and derived amino acid sequence (SEQ ID NO:26) of a portion of the 2.5 kb DNA insert of the plasmid subclone pGEMJLDc31/2.5, derived from clone λJLDc31, are shown in the Sequence Listings.

The DNA sequence of a portion of the 2.5 kb EcoRI insert of the plasmid pGEMJLDc31/2.5 is set forth in SEQ ID NO:25, contains an 912 bp open reading frame, as defined by nucleotides #52 through #963 of SEQ ID NO:25. As this sequence is derived from a genomic clone it is difficult to determine the boundary between the 5' extent of coding sequence and the 3' limit of intervening sequence (intron/non-coding sequence). The entire open reading frame (nucleotides #52 through #963 of SEQ ID NO:25) encodes a portion of the VL-1 protein of the invention of up to 304 amino acids.

Based on the knowledge of other BMP proteins and other proteins within the TGF-β family, it is predicted that the precursor polypeptide would be cleaved at the multibasic sequence Arg-Arg-Arg-Arg (SEQ ID NO:26, residues −4 to −1) in agreement with a proposed consensus proteolytic processing sequence of Arg-X-X-Arg (SEQ ID NO:26, residues −4 to −1). Cleavage of the VL-1 precursor polypeptide is expected to generate a 120 amino acid mature peptide beginning with the amino acid Thr at position #1 of SEQ ID NO:26. The processing of VL-1 into the mature form is expected to involve dimerization and removal of the N-terminal region in a manner analogous to the processing of the related protein TGF-β [Gentry et al., *Molec & Cell. Biol.*, 8:4162 (1988); Derynck et al. *Nature*, 316:701 (1985)].

It is contemplated therefore that the mature active species of VL-1 comprises a homodimer of two polypeptide subunits, each subunit comprising amino acids #1 to #120 of SEQ ID NO:26 with a predicted molecular weight of approximately 12,000 daltons. Further active species are contemplated comprising at least amino acids #19 to #119 or #120 of SEQ ID NO:26, thereby including the first and last conserved cysteine residue.

Using such a method, a clone encoding the mature human VL-1 (BMP-13) was obtained. The nucleotide sequence and corresponding amino acid sequence encoded by this clone are listed in the Sequence Listings at SEQ ID NO: 25 and 26, respectively.

EXAMPLE 2

Expression of BMP-12

In order to produce human BMP-12 proteins, the DNA encoding it is transferred into an appropriate expression vector and introduced into mammalian cells or other preferred eukaryotic or prokaryotic hosts by conventional genetic engineering techniques.

In order to produce the human BMP-12 protein in bacterial cells, the following procedure is employed.

Expression of BMP-12 in *E. coli*

An expression plasmid pALV1-781, for production of BMP-12 in *E. coli* was constructed which contains the following principal features. Nucleotides 1–2060 contain DNA sequences originating from the plasmid pUC-18 [Norrander et al., Gene 26:101–106 (1983)] including sequences containing the gene for β-lactamase which confers resistance to the antibiotic ampicillin in host *E. coli* strains, and a colE1-derived origin of replication. Nucleotides 2061–2221 contain DNA sequences for the major leftward promotor (pL) of bacteriophage λ [Sanger et al., J. Mol. Biol. 162:729–773 (1982)], including three operator sequences $0_L1$, $0_L2$ and $0_L3$. The operators are the binding sites for λcI repressor protein, intracellular levels of which control the amount of transcription initiation from pL. Nucleotides 2222–2723 contain a strong ribosome binding sequence included on a sequence derived from nucleotides 35566 to 35472 and 38137 to 38361 from bacteriophage lambda as described in Sanger et al., J. Mol. Biol. 162:729–773 (1982). Nucleotides 2724–3041 contain a DNA sequence encoding mature BMP-12 protein with all 3' untranslated sequence removed. The BMP-12 DNA sequences introduced into the pALV1-781 expression vector were modified at the 5' end to raise the A+T content without altering the coding capacity. These changes were made to increase the efficiency of translation initiated on the BMP-12 mRNA in *E. coli*. Nucleotides 3042–3058 provide a "Linker" DNA sequence containing restriction endonuclease sites. Nucleotides 3059–3127 provide a transcription termination sequence based on that of the *E. coli* asp A gene [Takagi et al., Nucl. Acids Res. 13:2063–2074 (1985)]. Nucleotides 3128–3532 are DNA sequences derived from pUC-18.

Plasmid pALV1-781 was transformed into the *E. coli* host strain GI724 (F, lacI$^q$, lacp$^{L8}$, ampC::λcI$^+$) by the procedure of Dagert and Ehrlich, Gene 6:23 (1979). GI724 (ATCC accession No. 55151) contains a copy of the wild-type λcI repressor gene stably integrated into the chromosome at the ampC locus, where it has been placed under the transcriptional control of *Salmonella typhimurium* trp promotor/operator sequences. In G1724, λCI protein is made only during growth in tryptophan-free media, such as minimal media or a minimal medium supplemented with casamino acids such as IMC, described above. Addition of tryptophan to a culture of GI724 will repress the trp promoter and turn off synthesis of λcI, gradually causing the induction of transcription from pL promoters if they are present in the cell.

Transformants were selected on 1.5% w/v agar plates containing IMC medium, which is composed of M9 medium [Miller, "Experiments in Molecular Genetics," Cold Spring Harbor Laboratory, New York (1972)] containing 1 mM MgSO$_4$ and supplemented with 0.5% w/v glucose, 0.2% w/v casamino acids and 100 µg/ml ampicillin. GI724 transformed with pALV1-781 was grown at 37° C. to an A$_{550}$ of 0.5 in IMC medium containing 100 µg/ml ampicillin. Tryptophan was then added to a final concentration of 100 µg/ml and the culture incubated for a further 4 hours. During this time BMP-12 protein accumulates within the "inclusion body" fraction.

Preparation of Protein Monomer 18 g of frozen cells were weighed out and resuspended in 60 ml of 100 mM Tris, 10 mM EDTA, 1 mM phenylmethylsulfonyl fluoride [PMSF], pH 8.3. Cells were lysed by 3 passes through a Microfluidizer™ [model #MCF 100 T]. The inclusion body pellet was obtained by centrifugation at 15,000 g at 4° C. for 20 minutes. The supernatant was decanted, and the pellet was washed with 100 ml of 100 mM Tris, 1.0 M NaCl, 10 mM EDTA, 1 mM PMSF, pH 8.3. The suspension was centrifuged again at 15,000 g at 4° C. for 10 minutes, and the supernatant decanted. The pellet was then washed with 100 ml of 100 mM Tris, 10 mM EDTA. 1% Triton X-100, 1 mM PMSF, pH 8.3. The suspension was centrifuged again at 15,000 g at 4° C. for 10 minutes, and the supernatant decanted. The pellet was resuspended with 50 ml of 20 mM Tris, 1 mM EDTA, 1 mM PMSF, pH 8.3, containing 1% DTT in a glass tissue homogenizer. Monomeric BMP-12 was then solubilized by acidification to pH 2.5 with glacial acetic acid. The soluble fraction was isolated by centrifugation at 15,000 g for 20 minutes at 4° C.

The supernatant from this centrifugation was collected and chromatographed over a Sephacryl S-100™ size exclusion column (83 cm×2.6 cm; ≈440 ml bed) in 20 ml increments. The Sephacryl S-100™ column was run with a mobile phase of 1% acetic acid at a flow rate of 1.4 ml/min. Fractions corresponding to BMP-12 monomer were detected by absorbance at 280 nm, and using a computer calculated extinction coefficient of $18200M^{-1}cm^{-1}$ and molecular weight (11667 daltons). This size exclusion column pooled material was used as starting material for refolding reactions.

As an alternative to the above, 1.0 g of cells stored at −80° C. are measured. Solution (3.4 ml 100 mM TRIS, 10 mM EDTA, pH 8.5) is added. The solution is vortexed until cells are well suspended. 40 µl 100 mM PMSF in isopropanol is added. The cells are lysed at 1000 psi in a French pressure cell. The inclusion bodies are centrifuged at 4° C. for 20 minutes in an Eppendorf microfuge to form pellets. The supernatants are decanted. To one pellet (out of 4 total) 1.0 ml degassed 8.0 M guanidine hydrochloride, 0.5 M TRIS, 5 mM EDTA, pH 8.5, containing 250 mM DTT is added. The pellet is dissolved and argon is blown over the liquid for 30 seconds. Next the solution is incubated at 37° C. for one hour. Insoluble material is pelleted for 2–3 minutes in an Eppendorf microfuge at 23° C. 0.5–1.0 ml of supernatant is injected onto a Supelco 2 cm guard cartridge (LC-304), and eluted with an acetonitrile gradient in 0.1% TFA from 1–70% over 35 minutes. BMP-12 elutes between 29 and 31 minutes. Fractions are pooled and the protein concentration determined by adsorbance at 280 nanometers versus 0.1% TFA, using the theoretical extinction coefficient based upon the amino acid content.

As a second alternate method to the above, frozen cell pellets obtained from the *E. coli* transformants as described above are thawed in 30 ml of TE8.3(100:10) buffer (100 mM Tris-HCl pH 8.3, 10 mM Na$_2$EDTA, 1 mM PMSF). Cells are lysed by three passes through a Microfluidizer™ [model #MCF 100 T]. The initial inclusion body material pellet is dissolved in 8 M guanidine-HCl, TE8.5(100:10) buffer (100 mM Tris-HCl pH 8.5, 10 mM Na$_2$EDTA which contained 100 mM DTT, and incubated at 37° C. for 1 hour. This material is centrifuged at 12,000×g for 15 minutes at room temperature.

Refolding of BMP-12 Protein Using CHAPS System

A sufficient volume of the BMP-12 pool is lyophilized to give 10 µg of protein. 5 µl of glass distilled water is added to redissolve the residue, then 100 µl of refold mix (50 mM Tris, 1.0 M NaCl, 2% 3-(3-chlolamido-propyl) dimethylammonio-1-propane-sulfate (CHAPS), 5 mM EDTA, 2 mM glutathione (reduced) 1 mM glutathione (oxidized); at pH of approximately 8.5). The solution is gently mixed and stored at 23° C. for 14 days. Dimer formation is assessed by running an aliquot on a Novex 16% tricine gel at 125 volts for 2.5 hours, followed by Coomassie Blue staining and destaining.

BMP-12 dimer was purified using a C4 analytical RP-HPLC (reversed phase-high performance liquid chromatography) column (Vydac 214TP54) which was equilibrated to 1% B buffer (diluted into A buffer) and was run over 35 minutes. during which the protein elutes, using the following gradient (A buffer=0.1% trifluoroacetic acid, B buffer=95% acetonitrile, 0.1% trifluoroacetic acid [TFA]), with a flow rate of 1 ml/min:

| | |
|---|---|
| 1–5 minutes | 20% B buffer |
| 5–10 minutes | 20–30% B buffer |
| 10–30 minutes | 30–50% B buffer |
| 30–35 minutes | 50–100% B buffer |

Protein was monitored by absorbance at 280 nm. Peak BMP-12 fractions (eluting between 29 and 31 minutes) were pooled. Purity was assessed by SDS-PAGE. The concentration was determined by absorbance at 280 nm, and using the computer calculated extinction coefficient and molecular weight as indicated above.

Expression of BMP-12 in Mammalian Cells

Another contemplated preferred expression system for biologically active recombinant human BMP-12 is stably transformed mammalian cells.

One skilled in the art can construct mammalian expression vectors by employing the sequence of SEQ ID NO:1, or other DNA sequences encoding BMP-12 proteins or other modified sequences and known vectors, such as pCD [Okayama et al., Mol. Cell Biol., 2:161–170 (1982)], pJL3, pJL4 [Gough et al., EMBO J., 4:645–653 (1985)] and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis [Moringa, et al., Biotechnology 84: 636 (1984). This removes bases 1075 to 1145 relative to the Hind III site near the SV40 origin of replication and enhancer sequences of pMT2. In addition it inserts a sequence containing the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform E. coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR. Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 [S. K. Jung, et al, J. Virol 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has a sequence which matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the BMP-12 DNA sequences. For instance, BMP-12 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of BMP-12 proteins. Additionally, the sequence of SEQ ID NO:1 or other sequences encoding BMP-12 proteins can be manipulated to express BMP-12 protein by isolating the mature-coding sequence-of nucleotides 571 to 882 of SEQ ID NO:1 and adding at the 5' end sequences encoding the complete propeptides of other BMP proteins.

For example, one skilled in the art can make a fusion protein in which the propeptide of BMP-2 is linked in operable fashion to the mature BMP-12 peptide by preparing a DNA vector in which the DNA sequence encoding the BMP-2 propeptide is linked in proper reading frame to the DNA sequence encoding the mature BMP-12 peptide. The DNA sequence of such a fusion protein is shown in SEQUENCE ID NO:27.

One skilled in the art can manipulate the sequences of SEQ ID NO:1 by eliminating or replacing the mammalian regulatory sequences flanking the coding sequence with bacterial sequences to create bacterial vectors for intracellular or extracellular expression by bacterial cells, as described above. As another example, the coding sequences could be further manipulated (e.g. ligated to other known linkers or modified by deleting non-coding sequences therefrom or altering nucleotides therein by other known techniques). The modified BMP-12 coding sequence could then be inserted into a known bacterial vector using procedures such as described in T. Taniguchi et al., Proc. Natl Acad. Sci. USA, 77:5230–5,233 (1980). This exemplary bacterial vector could then be transformed into bacterial host cells and a BMP-12 protein expressed thereby. For a strategy for producing extracellular expression of BMP-12 proteins in bacterial cells, see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-12 protein of the invention in mammalian cells may involve the construction of cells containing multiple copies of the heterologous BMP-12 gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a BMP-12 of the invention in operative association with other plasmid sequences enabling expression thereof and the DHFR expression plasmid pAdA26SV(A)3 [Kaufman and Sharp, *Mol. Cell. Biol.*, 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 uM MTX) as described in Kaufman et al., *Mol Cell Biol.*, 5:1750 (1983). Transformants are cloned, and biologically active BMP-12 expression is monitored by the Rosen-modified Sampath-Reddi rat assay described below in Example 5. BMP-12 expression should increase with increasing levels of MTX resistance. BMP-12 polypeptides are characterized using standard techniques known in the art such as pulse labeling with [35S] methionine or cysteine and polyacrylamide gel electrophoresis. Similar procedures can be followed to produce other related BMP-12 proteins.

EXAMPLE 3

Preparation of BMP-2 Propeptide/BMP-12 Mature Peptide Fusion

In order to construct a vector encoding the BMP-2 propeptide/BMP-12 mature peptide fusion, the following cloning procedure was used to fuse the two sequences together.

First, a DNA restriction enzyme fragment comprising the propeptide of human BMP-2 protein, comprising nucleotides 1 through 843 of SEQ ID NO:27 is cut from pBMP2ΔEMC. pBMP2ΔEMC is a plasmid derived from lambda U20S-39 (ATCC #40345) comprising the entire coding sequence for human BMP-2 protein with the non-translated 5' and 3' sequences of BMP-2 deleted from the vector. The 5' restriction enzyme used was Bgl II and it cuts pBMP2ΔEMC in the vector at nucleotide 979. The 3' restriction enzyme used was Mae II and it cuts pBMP2ΔEMC in the BMP-2 propeptide at nucleotide 1925, just short of the carboxy terminus. The resulting 954 base pair product was then gel isolated and gene cleaned. Second, a DNA restriction enzyme fragment comprising the 5' portion of the human BMP-12 mature peptide DNA sequence, is cut from pPCR1-1#2 V1-1 (ATCC #69517). The 5' restriction enzyme used was Eae I and it cuts pPCR1-1#2 V1-1 just 3' of N-terminus of the human BMP-12 mature peptide sequence. The resulting 259 base pair product was gel isolated and gene cleaned. Third, two DNA oligos were designed and synthesized, so that when annealed would form a tiny DNA fragment comprising fusion sequence of the extreme 3' end of the human BMP-2 propeptide and the 5' end of BMP-12 mature peptide. The DNA fragment has a 5' Mae II complimentary sticky end which anneals to the 3' restriction enzyme fragment comprising the human BMP-2 propeptide. The annealed oligo DNA fragment has a 3' Eae I complimentary sticky end which anneals to the 5' of the restriction enzyme fragment comprising the mature peptide of human BMP-12. The coding strand oligo is named B2/12 and is 13 base pairs long. Next, a DNA fragment encoding the 123 base pairs at the 3' end of the BMP-12 mature peptide fragment was obtained as follows. First, a DNA fragment comprising the propeptide of human BMP-2 protein, comprising nucleotides 1 through 846 is PCR amplified from pBMP2ΔEMC. The 5' primer (oligo 655a) anneals just 5' of the polylinker. The 3' primer (BMPpro3) anneals to the BMP-2 propeptide 3' end and introduces a Bgl II restriction enzyme site by silent sequence mutations. The resulting PCR product was cut with Sal I, which cleaves in the polylinker, and Bgl II. The 850 base pair restriction enzyme fragment (ending in amino acid sequence REKR) was gel isolated and gene cleaned. The BMP-12 mature peptide was PCR amplified using a 5' primer (oligo 5-1) encoding the Bgl II restriction enzyme site by silent sequence mutations, and annealing to the 5' end of a possible mature cleavage product, beginning with amino acid sequence SRCS. The 3' primer (V1-1 3) anneals to the BMP-12 mature peptide 3' end and introduces a Xba I restriction enzyme site after the stop codon. The resulting PCR product was cut with Bgl II and Xba I. The 321 base pair restriction enzyme-fragment was gel isolated and gene cleaned.

The two restriction fragments were three-way ligated into a previously SalI and XbaI cut vector. The resultant construct was sequenced to check for PCR induced errors and a silent C to T mutation was observed at base pair 185 in the propeptide. This plasmid was designated pREKRSRC. Then pREKRSRC was cut with BglII and NgoMI, and the vector fragment encompassing the last 123 base pairs of the BMP12 mature sequence was thereby isolated. The three restriction fragments and the annealed oligolinker were four-way ligated to yield pREKR-TAL with the BMP-2 propeptide with the mature cleavage site at the 3' end fused to the (TAL) 5' end of the BMP-12 mature peptide. The coding sequence of the resulting ligated vector is shown in SEQ ID NO:27.

EXAMPLE 4

Biological Activity of Expressed BMP-12

To measure the biological activity of the expressed BMP-12 proteins obtained in Example 2 above, the proteins are recovered from the cell culture and purified by isolating the BMP-12 proteins from other proteinaceous materials with which they are co-produced as well as from other contaminants. The purified protein may be assayed in accordance with the rat assay described below in Example 5.

Purification is carried out using standard techniques known to those skilled in the art.

Protein analysis is conducted using standard techniques such as SDS-PAGE acrylamide [Laemmli, *Nature* 227:680

EXAMPLE 5
Rosen Modified Sampath-Reddi Assay

A modified version of the rat ectopic implant assay described in Sampath and Reddi, *Proc. Natl. Acad. Sci. USA*, 80:6591–6595 (1983) is used to evaluate the activity of the BMP-12 proteins. This modified assay is herein called the Rosen-modified Sampath-Reddi assay. The assay has been widely used to evaluate the bone and cartilage-inducing activity of BMPs. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 10 days. A section of each implant is fixed and processed for histological analysis. 1 μm glycolmethacrylate sections are stained with Von Kossa and acid fuschin to score the amount of induced tendon/ligament-like tissue formation present in each implant.

BMP-12 was implanted in the rats in doses of 1, 5, 25 and 50 μg per implant for 10 days. BMP-2 at a dose of 5 μg was included as a positive control. For all doses of BMP-12 tested, no bone or cartilage formation was observed in the implants after ten days. Instead, the implants were filled with tissue resembling embryonic tendon, which is easily recognized by the presence of dense bundles of fibroblasts oriented in the same plane and packed tightly together. [Tendon/ligament-like tissue is described, for example, in Ham and Cormack, *Histology* (J B Lippincott Co. (1979), pp. 367–369, the disclosure of which is hereby incorporated by reference]. These findings were reproduced in a second set of assays in which tendon/ligament-like tissues was present in all BMP-12 containing implants. In contrast, the BMP-2 implants, as expected, showed cartilage and bone formation, but contained no tendon/ligament-like tissue.

The BMP-12 proteins and related proteins of this invention may be assessed for activity on this assay.

EXAMPLE 6

Using methods in accordance with the above examples, with minor modifications within the skill of the art, human MP52 protein and the murine homologue of BMP-13 protein were expressed and assayed for tendon/ligament-like tissue inducing activity. All proteins showed comparable results, similar to those described above for human BMP-12.

The foregoing descriptions detail presently preferred embodiments of the present invention. Numerous modifications and variations in practice thereof are expected to occur to those skilled in the-art upon consideration of these descriptions. Those modifications and variations are believed to be encompassed within the claims appended hereto. The disclosure of all references discussed herein are hereby incorporated by reference.

---

What is claimed is:

1. A purified Bone Morphogenetic Protein-12 related protein characterized by the ability to induce the formation of tendon/ligament-like tissue, wherein the protein is chosen from BMP-12, BMP-13, and MP52.

2. A pharmaceutical composition for tendon/ligament-like tissue healing and tissue repair, said composition comprising an effective amount of a Bone Morphogenetic Protein-12 related protein in a pharmaceutically acceptable vehicle, wherein the protein is chosen from SEQ ID NO:2, SEQ ID NO:4, and SEQ ID NO:26.

3. A pharmaceutical composition for tendon/ligament-like tissue repair, said composition comprising an effective amount of a Bone Morphogenetic Protein-12 related protein in a pharmaceutically acceptable vehicle, wherein the protein is chosen from BMP-12, BMP-13, and MP52.

4. A purified Bone Morphogenetic Protein-12 related protein characterized by the ability to induce the formation of tendon/ligament-like tissue, wherein the protein is chosen from SEQ ID NO:2, SEQ ID NO:4, and SEQ ID NO:26.

* * * * *

(12) EX PARTE REEXAMINATION CERTIFICATE (5536th)
United States Patent
Celeste et al.

(10) Number: US 6,719,968 C1
(45) Certificate Issued: *Sep. 26, 2006

(54) TENDON-INDUCING COMPOSITIONS

(75) Inventors: Anthony J. Celeste, Hudson, MA (US); John M. Wozney, Hudson, MA (US); Vicki A. Rosen, Brookline, MA (US); Neil M. Wolfman, Dover, MA (US); Gerald H. Thomsen, Port Jefferson, NY (US); Douglas A. Melton, Lexington, MA (US)

(73) Assignee: Genetics Institute, LLC, Madison, NJ (US)

Reexamination Request:
No. 90/007,448, Mar. 4, 2005

Reexamination Certificate for:
Patent No.: 6,719,968
Issued: Apr. 13, 2004
Appl. No.: 09/945,182
Filed: Aug. 31, 2001

(*) Notice: This patent is subject to a terminal disclaimer.

Related U.S. Application Data

(60) Division of application No. 08/808,324, filed on Feb. 28, 1997, now Pat. No. 6,284,872, which is a division of application No. 08/362,670, filed on Dec. 22, 1994, now Pat. No. 5,658,882, which is a continuation-in-part of application No. 08/217,780, filed on Mar. 25, 1994, now abandoned, and a continuation-in-part of application No. 08/164,103, filed on Dec. 7, 1993, now abandoned, and a continuation-in-part of application No. 08/333,576, filed on Nov. 2, 1994, now Pat. No. 6,027,919.

(51) Int. Cl.
*A61K 45/00* (2006.01)

(52) U.S. Cl. .............. 424/85.1; 530/350; 530/351; 530/395; 530/397; 530/399; 514/2; 514/5; 514/12

(58) Field of Classification Search ............ 530/350, 530/351, 395, 397, 399; 424/85.1; 514/2, 514/5, 12
See application file for complete search history.

(56) References Cited

U.S. PATENT DOCUMENTS

| | | | |
|---|---|---|---|
| 4,294,753 A | 10/1981 | Urist | 260/112 |
| 4,419,446 A | 12/1983 | Howley et al. | 435/68 |
| 4,434,094 A | 2/1984 | Seyedin et al. | 260/112 |
| 4,563,350 A | 1/1986 | Nathan et al. | 424/95 |
| 4,627,982 A | 12/1986 | Seyedin et al. | 424/95 |
| 4,761,471 A | 8/1988 | Urist | 530/350 |
| 4,774,228 A | 9/1988 | Seyedin et al. | 514/21 |
| 4,774,322 A | 9/1988 | Seyedin et al. | 530/353 |
| 4,804,744 A | 2/1989 | Sen | 530/350 |
| 4,877,864 A | 10/1989 | Wang et al. | 530/350 |
| 4,968,590 A | 11/1990 | Kuberasampath et al. | 530/326 |
| 5,013,649 A | 5/1991 | Wang et al. | 435/69.1 |
| 5,106,748 A | 4/1992 | Wozney et al. | 435/252.3 |
| 5,108,922 A | 4/1992 | Wang et al. | 435/240.2 |
| 5,116,738 A | 5/1992 | Wang et al. | 435/69.1 |
| 5,141,905 A | 8/1992 | Rosen et al. | 435/69.1 |
| 5,168,050 A | 12/1992 | Hammonds, Jr. et al. | 435/69.1 |
| 5,187,076 A | 2/1993 | Wozney et al. | 435/69.1 |
| 5,447,725 A | 9/1995 | Damani et al. | 424/435 |
| 5,455,041 A | 10/1995 | Genco et al. | 424/435 |
| 5,658,882 A | 8/1997 | Celeste et al. | 514/12 |
| 5,986,058 A | 11/1999 | Lee et al. | 530/351 |
| 6,027,919 A | 2/2000 | Celeste et al. | 435/69.7 |
| 6,284,872 B1 | 9/2001 | Celeste et al. | 530/399 |

FOREIGN PATENT DOCUMENTS

| | | |
|---|---|---|
| CA | 2017466 | 5/1990 |
| EP | 0 177 343 A1 | 9/1986 |
| EP | 0 336 760 A2 | 10/1989 |
| EP | 0 409 472 A1 | 1/1991 |
| EP | 0 416 578 A2 | 3/1991 |
| WO | WO 84/01106 | 3/1984 |
| WO | WO 91/18047 | 11/1991 |
| WO | WO 91/18098 | 11/1991 |
| WO | WO 93/00050 | 1/1993 |
| WO | WO 93/00432 | 1/1993 |
| WO | WO 93/16099 | 8/1993 |
| WO | WO 9316099 A2 * | 8/1993 |
| WO | WO 95/01801 | 1/1995 |
| WO | WO 95/01802 | 1/1995 |

OTHER PUBLICATIONS

Storm et al. Nature (London, UK) vol. 368(6472) (Apr. 14, 1994).*

Bowie et al., "Deciphering the Message in Protein Sequences Tolerance to Amino Acid Substitutions," *Science*, 247:1306–1310 (1990).

Chang et al., "Cartilage–derived Morphogenetic Proteins," *J. Biol. Chem*, 269:28227–28234 (1994).

Dagert et al., "Prolonged Incubation in Calcium Chloride Improves the Competence of *Escherichia coli* Cells," *Gene*, 6:23 (1979).

Derynck et al., "Human transforming growth factor–β complementary DNA sequence and expression in normal and transformed cells," *Nature*, 316:701 (1985).

Gentry et al., "Molecular Events in the Processing of Recombinant Type 1 Pre–Pro–Transforming Growth Factor Beta to the Mature Polypeptide," *Molec. & Cell. Biol.*, 8:4162 (1988).

Gething et al., "Cell–surface expression of influenza haemagglutinin from a cloned DNA copy of the RNA gene," *Nature*, 293:620–625 (1981).

Gough et al., "Structure and expression of the mRNA for murine granulocyte–macrophage colony stimulating factor," *The EMBO Journal*, 4(3):645–653 (1985).

Ham et al., "Tendons, Ligaments, and Cartilage," *Histology*, JB Lippincott Co., pp. 367–369 (1979).

(Continued)

*Primary Examiner*—Bennett Celsa

(57) ABSTRACT

Compositions of proteins with tendon/ligament-like tissue inducing activity are disclosed. The compositions are useful in the treatment of tendinitis and tendon or ligament defects and in related tissue repair.

OTHER PUBLICATIONS

Jang et al., "Initiation of Protein Synthesis by Internal Entry of Ribosomes into the 5' Nontranslated Region of Encephalomyocarditis Virus RNA In Vivo," *J. of Virology*, 63(4):1651–1660 (1989).

Joyce et al., "Tendon adhesion formation is stimulated by exogenous growth factors," *J. Cell Biol.*, 17E (Suppl), 136:Abstract R504 (1993).

Kaufman, et al., "Coamplification and Coexpression of Human Tissue–Type Plasminogen Activator and Murine Dihydrofolate Reductase Sequences in Chinese Hamster Ovary Cells," *Mol. Cell. Biol.*, 5(7):1750–1759 (1985).

Kaufman, "Identification of the components necessary for adenovirus translational control and their utilization in cDNA expression vectors," *Proc. Natl. Acad. Sci. USA*, 82:689–693 (1985).

Kaufman, et al., "Improved vectors for stable expression of foreign genes in mammalian cells by use of the untranslated leader sequence from EMC virus," *Nucl. Acids Res.*, 19(16):4485–4490 (1991).

Kaufman et al., "Construction of a Modular Dihydrofolate Reductase cDNA Gene: Analysis of Signals Utilized for Efficient Expression," *Mol. Cell Biol.*, 2: 1304–1319 (1982).

Laemmli, U.K., "Cleavage of Structural Proteins during the Assembly of the Head of Bacteriophage T4," *Nature*, 227:680–685 (1970).

LaVallie et al., "A Thioredoxin Gene Fusion Expression System That Circumvents Inclusion Body Formation in the *E. coli* Cytoplasm," Bio/Technology, 11:187–193 (1993).

Maniatis et al., Molecular Cloning (A Laboratory Manual), Cold Spring Harbor Laboratory, pp. 387–389 (1982).

Miller, et al., "An Insect Baculovirus Host–Vector System for High–Level Expression of Foreign Genes," Genetic Engineering: Principles and Methods, 8:277–298 (1986).

Miller, "Experiments in Molecular Genetics," Cold Spring Harbor Laboratory, New York, 1972.

Morinaga et al., "Improvement of Oligonucleotide–directed Site–specific Mutagenesis using Double–stranded Plasmid DNA," *Biotechnology*, 84:636 (1984).

Ngo et al., "Computational Complexity, Protein Structure Prediction, and the Levinthal Paradox," The Protein Folding Problem and Tertiary Structure Prediction, Merz et al., eds., Birkhauser, Boston, pp. 491–495 (1994).

Norrander et al., "Construction of improved M13 vectors using oligodeoxynucleotide–directed mutagenesis," *Gene*, 26:101–106 (1983).

Oakley, et al., "A Simplified Ultrasensitive Silver Stain for Detecting Proteins in Polyacrylamide Gels," *Analytical Biochemistry*, 105:361–363 (1980).

Okayama, et al., "High–Efficiency Cloning of Full–Length cDNA," *Mol. Cell. Biol.*, 2(2):161–170 (1982).

Ozkaynak et al., "OP–1 cDNA encodes an osteogenic protein in the TGF–β family," EMBO J., 9(7):2085–2093 (1990).

Sampath et al., "Homology of bone–inductive proteins from human, monkey, bovine, and rat extracellular matrix," PNAS, 80:6591–6595 (1983).

Sampath et al., "Isolation of osteogenin, an extracellular matrix–associated, bone–inductive protein, by heparin affinity chromatography," PNAS, 84:7109–7113 (1987).

Sanger et al., "Nucleotide Sequence of Bacteriophage λ DNA," J. Mol. Biol., 162:729–773 (1982).

Storm et al., "Limb alterations in brachypodism mice due to mutations in a new member of the TGFβ–superfamily," Nature, 368:639–642 (1994).

Takagi et al., "Cloning and nucleotide sequence of the aspartase gene of *Escherichia coli*" Nucl. Acids Res., 13:2063–2074 (1985).

Taniguchi et al., "Expression of the human fibroblast interferon gene in *Escherichia coli*," Proc. Natl. Acad. Sci. USA, 77(9):5230–5233 (1980).

Towbin et al., "Electrophoretic transfer of proteins from polyacrylamide gels to nitrocellulose sheets: Procedure and some applications," PNAS, 76(9):4350–4354 (1979).

Urist et al., "Bone Cell Differentiation and Growth Factors," Science, 220:680–686 (1983).

Wells, "Additivity of Mutational Effects in Proteins," in *Perspectives in Biochemistry*, 29:8509–8517 (1990).

Wong, et al., "Human GM–CSF: Molecular Cloning of the Complementary DNA and Purificaion of the Natural and Recombinant Proteins," *Science*, 228:810–815 (1985).

Wozney, "The Bone Morphogenetic Protein Family and Osteogenesis," *Molecular Reproduction and Development*, 32:160–167 (1992).

Wozney, "Bone Morphogenetic Proteins," *Progress in Growth Factor Research*, 1:267–280 (1989).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 3 and 4 are determined to be patentable as amended.

New claims 5, 6, 7 and 8 are added and determined to be patentable.

1. A purified Bone Morphogenetic Protein-12 [related] protein characterized by the ability to induce the formation of tendon/ligament-like tissue[, wherein the protein is chosen from BMP-12, BMP-13, and MP52].

2. A pharmaceutical composition for tendon/ligament-like tissue healing and tissue repair, said composition comprising an effective amount of a Bone Morphogenetic Protein-12 related protein in a pharmaceutically acceptable vehicle, wherein the protein is chosen from SEQ ID NO:2[, SEQ ID NO:4,] and SEQ ID NO:26.

3. A pharmaceutical composition for tendon/ligament-like tissue repair, said composition comprising an effective amount of a Bone Morphogenetic Protein-12 [related] protein in a pharmaceutically acceptable vehicle[, wherein the protein is chosen from BMP-12, BMP-13, and MP52].

4. A purified [Bone Morphogenetic Protein-12 related] protein characterized by the ability to induce the formation of tendon/ligament-like tissue, wherein the protein is chosen from SEQ ID NO:2[, SEQ ID NO:4,] and SEQ ID NO:26.

5. *The pharmaceutical composition of claim 2, wherein the protein is SEQ ID NO:2.*

6. *The pharmaceutical composition of claim 2, wherein the protein is SEQ ID NO:26.*

7. *The protein of claim 4, wherein the protein is SEQ ID NO:2.*

8. *The protein of claim 4, wherein the protein is SEQ ID NO:26.*

\* \* \* \* \*

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
      (A) LENGTH: 926 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Homo sapiens (vii) IMMEDIATE SOURCE:
      (B) CLONE: v1-1

(ix) FEATURE:
      (A) NAME/KEY: mat_peptide
      (B) LOCATION: 571..882

(ix) FEATURE:
      (A) NAME/KEY: CDS
      (B) LOCATION: 1..882

(xi) SEQUENCE DESCRIPTION: SEQ ID NO: 1:

```
GCG CGT AAT ACG ACT CAC TAT AGG GCG AAT TGG GTA CGG GGC CCA GGC      48
Ala Arg Asn Thr Thr His Tyr Arg Ala Asn Trp Val Arg Gly Pro Gly
-190             -185             -180             -175
```

```
AGC TGG ACT TCT CCG CCG TTG CTG CTG CTG TCC ACG TGC CCG GGC GCC    96
Ser Trp Thr Ser Pro Pro Leu Leu Leu Leu Ser Thr Cys Pro Gly Ala
            -170            -165            -160

GCC CGA GCG CCA CGC CTG CTG TAC TCG CGG GCA GCT GAG CCC CTA GTC   144
Ala Arg Ala Pro Arg Leu Leu Tyr Ser Arg Ala Ala Glu Pro Leu Val
            -155            -150            -145

GGT CAG CGC TGG GAG GCG TTC GAC GTG GCG GAC GCC ATG AGG CGC CAC   192
Gly Gln Arg Trp Glu Ala Phe Asp Val Ala Asp Ala Met Arg Arg His
            -140            -135            -130

CGT CGT GAA CCG CGC CCC CCC CGC GCG TTC TGC CTC TTG CTG CGC GCA   240
Arg Arg Glu Pro Arg Pro Pro Arg Ala Phe Cys Leu Leu Leu Arg Ala
        -125            -120            -115

GTG GCA GGC CCG GTG CCG AGC CCG TTG GCA CTG CGG CGA CTG GGC TTC   288
Val Ala Gly Pro Val Pro Ser Pro Leu Ala Leu Arg Arg Leu Gly Phe
-110            -105            -100                    -95

GGC TGG CCG GGC GGA GGG GGC TCT GCG GCA GAG GAG CGC GCG GTG CTA   336
Gly Trp Pro Gly Gly Gly Gly Ser Ala Ala Glu Glu Arg Ala Val Leu
            -90             -85             -80

GTC GTC TCC TCC CGC ACG CAG AGG AAA GAG AGC TTA TTC CGG GAG ATC   384
Val Val Ser Ser Arg Thr Gln Arg Lys Glu Ser Leu Phe Arg Glu Ile
            -75             -70             -65

CGC GCC CAG GCC CGC GCG CTC GGG GCC GCT CTG GCC TCA GAG CCG CTG   432
Arg Ala Gln Ala Arg Ala Leu Gly Ala Ala Leu Ala Ser Glu Pro Leu
            -60             -55             -50

CCC GAC CCA GGA ACC GGC ACC GCG TCG CCA AGG GCA GTC ATT GGC GGC   480
Pro Asp Pro Gly Thr Gly Thr Ala Ser Pro Arg Ala Val Ile Gly Gly
            -45             -40             -35

CGC AGA CGG AGG AGG ACG GCG TTG GCC GGG ACG CGG ACA GCG CAG GGC   528
Arg Arg Arg Arg Arg Thr Ala Leu Ala Gly Thr Arg Thr Ala Gln Gly
-30             -25             -20                     -15

AGC GGC GGG GGC GCG GGC CGG GGC CAC GGG CGC AGG GGC CGG AGC CGC   576
Ser Gly Gly Gly Ala Gly Arg Gly His Gly Arg Arg Gly Arg Ser Arg
            -10              -5                      1

TGC AGC CGC AAG CCG TTG CAC GTG GAC TTC AAG GAG CTC GGC TGG GAC   624
Cys Ser Arg Lys Pro Leu His Val Asp Phe Lys Glu Leu Gly Trp Asp
         5              10              15

GAC TGG ATC ATC GCG CCG CTG GAC TAC GAG GCG TAC CAC TGC GAG GGC   672
Asp Trp Ile Ile Ala Pro Leu Asp Tyr Glu Ala Tyr His Cys Glu Gly
        20              25              30

CTT TGC GAC TTC CCT TTG CGT TCG CAC CTC GAG CCC ACC AAC CAT GCC   720
Leu Cys Asp Phe Pro Leu Arg Ser His Leu Glu Pro Thr Asn His Ala
 35              40              45              50

ATC ATT CAG ACG CTG CTC AAC TCC ATG GCA CCA GAC GCG GCG CCG GCC   768
Ile Ile Gln Thr Leu Leu Asn Ser Met Ala Pro Asp Ala Ala Pro Ala
            55              60              65

TCC TGC TGT GTG CCA GCG CGC CTC AGC CCC ATC AGC ATC CTC TAC ATC   816
Ser Cys Cys Val Pro Ala Arg Leu Ser Pro Ile Ser Ile Leu Tyr Ile
            70              75              80

GAC GCC GCC AAC AAC GTT GTC TAC AAG CAA TAC GAG GAC ATG GTG GTG   864
Asp Ala Ala Asn Asn Val Val Tyr Lys Gln Tyr Glu Asp Met Val Val
            85              90              95

GAG GCC TGC GGC TGC AGG TAGCGCGCGG GCCGGGAGG GGGCAGCCAC           912
Glu Ala Cys Gly Cys Arg
        100

GCGGCCGAGG ATCC                                                   926

(2) INFORMATION FOR SEQ ID NO: 2:

(i) SEQUENCE CHARACTERISTICS:
        (A) LENGTH: 294 amino acids
```

(B) TYPE: amino acid
            (D) TOPOLOGY: linear (ii) MOLECULE TYPE: protein (xi) SEQUENCE DESCRIPTION: SEQ ID NO: 2:

Ala Arg Asn Thr Thr His Tyr Arg Ala Asn Trp Val Arg Gly Pro Gly
-190            -185            -180            -175

Ser Trp Thr Ser Pro Pro Leu Leu Leu Ser Thr Cys Pro Gly Ala
            -170            -165            -160

Ala Arg Ala Pro Arg Leu Leu Tyr Ser Arg Ala Ala Glu Pro Leu Val
        -155            -150            -145

Gly Gln Arg Trp Glu Ala Phe Asp Val Ala Asp Ala Met Arg Arg His
        -140            -135            -130

Arg Arg Glu Pro Arg Pro Pro Arg Ala Phe Cys Leu Leu Arg Ala
    -125            -120            -115

Val Ala Gly Pro Val Pro Ser Pro Leu Ala Leu Arg Arg Leu Gly Phe
-110            -105            -100                    -95

Gly Trp Pro Gly Gly Gly Ser Ala Ala Glu Glu Arg Ala Val Leu
            -90            -85            -80

Val Val Ser Ser Arg Thr Gln Arg Lys Glu Ser Leu Phe Arg Glu Ile
            -75            -70            -65

Arg Ala Gln Ala Arg Ala Leu Gly Ala Ala Leu Ala Ser Glu Pro Leu
    -60            -55            -50

Pro Asp Pro Gly Thr Gly Thr Ala Ser Pro Arg Ala Val Ile Gly Gly
    -45            -40            -35

Arg Arg Arg Arg Arg Thr Ala Leu Ala Gly Thr Arg Thr Ala Gln Gly
-30            -25            -20            -15

Ser Gly Gly Gly Ala Gly Arg Gly His Gly Arg Arg Gly Arg Ser Arg
            -10            -5                    1

Cys Ser Arg Lys Pro Leu His Val Asp Phe Lys Glu Leu Gly Trp Asp
        5            10            15

Asp Trp Ile Ile Ala Pro Leu Asp Tyr Glu Ala Tyr His Cys Glu Gly
        20            25            30

Leu Cys Asp Phe Pro Leu Arg Ser His Leu Glu Pro Thr Asn His Ala
35            40            45            50

Ile Ile Gln Thr Leu Leu Asn Ser Met Ala Pro Asp Ala Ala Pro Ala
            55            60            65

Ser Cys Cys Val Pro Ala Arg Leu Ser Pro Ile Ser Ile Leu Tyr Ile
            70            75            80

Asp Ala Ala Asn Asn Val Val Tyr Lys Gln Tyr Glu Asp Met Val Val
            85            90            95

Glu Ala Cys Gly Cys Arg
    100

(2) INFORMATION FOR SEQ ID NO: 3:

(i) SEQUENCE CHARACTERISTICS:
        (A) LENGTH: 1207 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (vii) IMMEDIATE SOURCE:

(B) CLONE: MP52

(ix) FEATURE:
    (A) NAME/KEY: CDS
    (B) LOCATION: 845..1204

(xi) SEQUENCE DESCRIPTION: SEQ ID NO: 3:

```
ACCGGGCGGC CCTGAACCCA AGCCAGGACA CCCTCCCCAA ACAAGGCAGG CTACAGCCCG      60

GACTGTGACC CCAAAAGGAC AGCTTCCCGG AGGCAAGGCA CCCCCAAAAG CAGGATCTGT     120

CCCCAGCTCC TTCCTGCTGA AGAAGGCCAG GGAGCCCGGG CCCCCACGAG AGCCCAAGGA     180

GCCGTTTCGC CCACCCCCCA TCACACCCCA CGAGTACATG CTCTCGCTGT ACAGGACGCT     240

GTCCGATGCT GACAGAAAGG GAGGCAACAG CAGCGTGAAG TTGGAGGCTG GCCTGGCCAA     300

CACCATCACC AGCTTTATTG ACAAAGGGCA AGATGACCGA GGTCCCGTGG TCAGGAAGCA     360

GAGGTACGTG TTTGACATTA GTGCCCTGGA GAAGGATGGG CTGCTGGGGG CCGAGCTCCG     420

GATCTTGCGG AAGAAGCCCT CGGACACGGC CAAGCCAGCG GCCCCGGAG GCGGGCGGGC      480

TGCCCAGCTG AAGCTGTCCA GCTGCCCCAG CGGCCGGCAG CCGGCCTCCT TGCTGGATGT     540

GCGCTCCGTG CCAGGCCTGG ACGGATCTGG CTGGGAGGTG TTCGACATCT GGAAGCTCTT     600

CCGAAACTTT AAGAACTCGG CCCAGCTGTG CCTGGAGCTG GAGGCCTGGG AACGGGGCAG     660

GGCCGTGGAC CTCCGTGGCC TGGGCTTCGA CCGCGCCGCC CGGCAGGTCC ACGAGAAGGC     720

CCTGTTCCTG GTGTTTGGCC GCACCAAGAA ACGGGACCTG TTCTTTAATG AGATTAAGGC     780

CCGCTCTGGC CAGGACGATA AGACCGTGTA TGAGTACCTG TTCAGCCAGC GGCGAAAACG     840

GCGG GCC CCA CTG GCC ACT CGC CAG GGC AAG CGA CCC AGC AAG AAC CTT     889
     Ala Pro Leu Ala Thr Arg Gln Gly Lys Arg Pro Ser Lys Asn Leu
      1               5                  10                  15

AAG GCT CGC TGC AGT CGG AAG GCA CTG CAT GTC AAC TTC AAG GAC ATG      937
Lys Ala Arg Cys Ser Arg Lys Ala Leu His Val Asn Phe Lys Asp Met
             20                  25                  30

GGC TGG GAC GAC TGG ATC ATC GCA CCC CTT GAG TAC GAG GCT TTC CAC      985
Gly Trp Asp Asp Trp Ile Ile Ala Pro Leu Glu Tyr Glu Ala Phe His
         35                  40                  45

TGC GAG GGG CTG TGC GAG TTC CCA TTG CGC TCC CAC CTG GAG CCC ACG     1033
Cys Glu Gly Leu Cys Glu Phe Pro Leu Arg Ser His Leu Glu Pro Thr
     50                  55                  60

AAT CAT GCA GTC ATC CAG ACC CTG ATG AAC TCC ATG GAC CCC GAG TCC     1081
Asn His Ala Val Ile Gln Thr Leu Met Asn Ser Met Asp Pro Glu Ser
 65                  70                  75

ACA CCA CCC ACC TGC TGT GTG CCC ACG CGG CTG AGT CCC ATC AGC ATC     1129
Thr Pro Pro Thr Cys Cys Val Pro Thr Arg Leu Ser Pro Ile Ser Ile
 80                  85                  90                  95

CTC TTC ATT GAC TCT GCC AAC AAC GTG GTG TAT AAG CAG TAT GAG GAC     1177
Leu Phe Ile Asp Ser Ala Asn Asn Val Val Tyr Lys Gln Tyr Glu Asp
                100                 105                 110

ATG GTC GTG GAG TCG TGT GGC TGC AGG TAG                             1207
Met Val Val Glu Ser Cys Gly Cys Arg
                115                 120
```

(2) INFORMATION FOR SEQ ID NO: 4:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO: 4:

```
Ala Pro Leu Ala Thr Arg Gln Gly Lys Arg Pro Ser Lys Asn Leu Lys
 1               5                  10                  15

Ala Arg Cys Ser Arg Lys Ala Leu His Val Asn Phe Lys Asp Met Gly
                20                  25                  30

Trp Asp Trp Ile Ile Ala Pro Leu Glu Tyr Glu Ala Phe His Cys
            35                  40                  45

Glu Gly Leu Cys Glu Phe Pro Leu Arg Ser His Leu Glu Pro Thr Asn
     50                  55                  60

His Ala Val Ile Gln Thr Leu Met Asn Ser Met Asp Pro Glu Ser Thr
 65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
                100                 105                 110

Val Val Glu Ser Cys Gly Cys Arg
        115                 120
```

(2) INFORMATION FOR SEQ ID NO: 5:

(i) SEQUENCE CHARACTERISTICS:
        (A) LENGTH: 128 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
       (A) ORGANISM: Homo Sapiens (vii) IMMEDIATE SOURCE:
       (B) CLONE: V1-1 fragment (ix) FEATURE:
       (A) NAME/KEY: CDS
       (B) LOCATION: 28..102

(xi) SEQUENCE DESCRIPTION: SEQ ID NO: 5:

```
GGATCCTGGA AGGATTGGAT CATTGCG CCG CTG GAC TAC GAG GCG TAC CAC           51
                             Pro Leu Asp Tyr Glu Ala Tyr His
                              1               5

TGC GAG GGC CTT TGC GAC TTC CCT TTG CGT TCG CAC CTC GAG CCC ACC          99
Cys Glu Gly Leu Cys Asp Phe Pro Leu Arg Ser His Leu Glu Pro Thr
         10                  15                  20

AAC CACGCTATAG TCCAAACCTT TCTAGA                                        128
Asn

25
```

(2) INFORMATION FOR SEQ ID NO: 6:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO: 6:

```
Pro Leu Asp Tyr Glu Ala Tyr His Cys Glu Gly Leu Cys Asp Phe Pro
 1               5                  10                  15

Leu Arg Ser His Leu Glu Pro Thr Asn
                20                  25
```

(2) INFORMATION FOR SEQ ID NO: 7:

(i) SEQUENCE CHARACTERISTICS:
        (A) LENGTH: 128 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo Sapiens (vii) IMMEDIATE SOURCE:
        (B) CLONE: VL-1

(ix) FEATURE:
        (A) NAME/KEY: CDS
        (B) LOCATION: 28..102

(xi) SEQUENCE DESCRIPTION: SEQ ID NO: 7:

```
GGATCCTGGG ATGACTGGAT TATGGCG CCG CTG GAC TAC GAG GCG TAC CAC        51
                                Pro Leu Asp Tyr Glu Ala Tyr His
                                 1               5

TGC GAG GGT GTA TGC GAC TTC CCG CTG CGC TCG CAC CTG GAG CCC ACC      99
Cys Glu Gly Val Cys Asp Phe Pro Leu Arg Ser His Leu Glu Pro Thr
     10              15                  20

AAC CACGCCATGC TACAAACGCT TCTAGA                                    128
Asn
 25
```

(2) INFORMATION FOR SEQ ID NO: 8:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO: 8:

```
Pro Leu Asp Tyr Glu Ala Tyr His Cys Glu Gly Val Cys Asp Phe Pro
 1               5                  10                  15

Leu Arg Ser His Leu Glu Pro Thr Asn
             20                  25
```

(2) INFORMATION FOR SEQ ID NO: 9:

(i) SEQUENCE CHARACTERISTICS:
        (A) LENGTH: 3585 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: pALV1-781

(xi) SEQUENCE DESCRIPTION: SEQ ID NO: 9:

```
CTAACTACCC AACTCAAAAA AAAAAAAAAA AAAAACCCCC TCTAACCCCC ATTGACGAAA     60

GGGCCTCGTG ATACGCCTAT TTTTATAGGT TAATGTCATG ATAATAATGG TTTCTTAGAC    120

GTCAGGTGGC ACTTTTCGGG GAAATGTGCG CGGAACCCCT ATTTGTTTAT TTTTCTAAAT    180

ACATTCAAAT ATGTATCCGC TCATGAGACA ATAACCCTGA TAAATGCTTC AATAATATTG    240

AAAAAGGAAG AGTATGAGTA TTCAACATTT CCGTGTCGCC CTTATTCCCT TTTTTGCGGC    300
```

```
ATTTTGCCTT CCTGTTTTTG CTCACCCAGA AACGCTGGTG AAAGTAAAAG ATGCTGAAGA      360

TCAGTTGGGT GCACGAGTGG GTTACATCGA ACTGGATCTC AACAGCGGTA AGATCCTTGA      420

GAGTTTTCGC CCCGAAGAAC GTTTTCCAAT GATGAGCACT TTTAAAGTTC TGCTATGTGG      480

CGCGGTATTA TCCCGTATTG ACGCCGGGCA AGAGCAACTC GGTCGCCGCA TACACTATTC      540

TCAGAATGAC TTGGTTGAGT ACTCACCAGT CACAGAAAAG CATCTTACGG ATGGCATGAC      600

AGTAAGAGAA TTATGCAGTG CTGCCATAAC CATGAGTGAT AACACTGCGG CCAACTTACT      660

TCTGACAACG ATCGGAGGAC CGAAGGAGCT AACCGCTTTT TTGCACAACA TGGGGGATCA      720

TGTAACTCGC CTTGATCGTT GGGAACCGGA GCTGAATGAA GCCATACCAA ACGACGAGCG      780

TGACACCACG ATGCCTGTAG CAATGGCAAC AACGTTGCGC AAACTATTAA CTGGCGAACT      840

ACTTACTCTA GCTTCCCGGC AACAATTAAT AGACTGGATG GAGGCGGATA AAGTTGCAGG      900

ACCACTTCTG CGCTCGGCCC TTCCGGCTGG CTGGTTTATT GCTGATAAAT CTGGAGCCGG      960

TGAGCGTGGG TCTCGCGGTA TCATTGCAGC ACTGGGGCCA GATGGTAAGC CCTCCCGTAT     1020

CGTAGTTATC TACACGACGG GGAGTCAGGC AACTATGGAT GAACGAAATA GACAGATCGC     1080

TGAGATAGGT GCCTCACTGA TTAAGCATTG GTAACTGTCA GACCAAGTTT ACTCATATAT     1140

ACTTTAGATT GATTTAAAAC TTCATTTTTA ATTTAAAAGG ATCTAGGTGA AGATCCTTTT     1200

TGATAATCTC ATGACCAAAA TCCCTTAACG TGAGTTTTCG TTCCACTGAG CGTCAGACCC     1260

CGTAGAAAAG ATCAAAGGAT CTTCTTGAGA TCCTTTTTTT CTGCGCGTAA TCTGCTGCTT     1320

GCAAACAAAA AAACCACCGC TACCAGCGGT GGTTTGTTTG CCGGATCAAG AGCTACCAAC     1380

TCTTTTTCCG AAGGTAACTG GCTTCAGCAG AGCGCAGATA CCAAATACTG TCCTTCTAGT     1440

GTAGCCGTAG TTAGGCCACC ACTTCAAGAA CTCTGTAGCA CCGCCTACAT ACCTCGCTCT     1500

GCTAATCCTG TTACCAGTGG CTGCTGCCAG TGGCGATAAG TCGTGTCTTA CCGGGTTGGA     1560

CTCAAGACGA TAGTTACCGG ATAAGGCGCA GCGGTCGGGC TGAACGGGGG GTTCGTGCAC     1620

ACAGCCCAGC TTGGAGCGAA CGACCTACAC CGAACTGAGA TACCTACAGC GTGAGCATTG     1680

AGAAAGCGCC ACGCTTCCCG AAGGGAGAAA GGCGGACAGG TATCCGGTAA GCGGCAGGGT     1740

CGGAACAGGA GAGCGCACGA GGGAGCTTCC AGGGGGAAAC GCCTGGTATC TTTATAGTCC     1800

TGTCGGGTTT CGCCACCTCT GACTTGAGCG TCGATTTTTG TGATGCTCGT CAGGGGGCG      1860

GAGCCTATGG AAAAACGCCA GCAACGCGGC CTTTTTACGG TTCCTGGCCT TTTGCTGGCC     1920

TTTTGCTCAC ATGTTCTTTC CTGCGTTATC CCCTGATTCT GTGGATAACC GTATTACCGC     1980

CTTTGAGTGA GCTGATACCG CTCGCCGCAG CCGAACGACC GAGCGCAGCG AGTCAGTGAG     2040

CGAGGAAGCG GAAGAGCGCC CAATACGCAA ACCGCCTCTC CCCGCGCGTT GGCCGATTCA     2100

TTAATGCAGA ATTGATCTCT CACCTACCAA ACAATGCCCC CCTGCAAAAA ATAAATTCAT     2160

ATAAAAAACA TACAGATAAC CATCTGCGGT GATAAATTAT CTCTGGCGGT GTTGACATAA     2220

ATACCACTGG CGGTGATACT GAGCACATCA GCAGGACGCA CTGACCACCA TGAAGGTGAC     2280

GCTCTTAAAA ATTAAGCCCT GAAGAAGGGC AGCATTCAAA GCAGAAGGCT TTGGGGTGTG     2340

TGATACGAAA CGAAGCATTG GCCGTAAGTG CGATTCCGGA TTAGCTGCCA ATGTGCCAAT     2400

CGCGGGGGT TTTCGTTCAG GACTACAACT GCCACACACC ACCAAAGCTA ACTGACAGGA     2460

GAATCCAGAT GGATGCACAA ACACGCCGCC GCGAACGTCG CGCAGAGAAA CAGGCTCAAT     2520

GGAAAGCAGC AAATCCCCTG TTGGTTGGGG TAAGCGCAAA ACCAGTTCCG AAAGATTTTT     2580

TTAACTATAA ACGCTGATGG AAGCGTTTAT GCGGAAGAGG TAAAGCCCTT CCCGAGTAAC     2640
```

```
AAAAAAACAA CAGCATAAAT AACCCCGCTC TTACACATTC CAGCCCTGAA AAAGGGCATC    2700

AAATTAAACC ACACCTATGG TGTATGCATT TATTTGCATA CATTCAATCA ATTGTTATCT    2760

AAGGAAATAC TTACATATGT CTCGTTGTTC TCGTAAACCA CTGCATGTAG ATTTTAAAGA    2820

GCTCGGCTGG GACGACTGGA TCATCGCGCC GCTGGACTAC GAGGCGTACC ACTGCGAGGG    2880

CCTTTGCGAC TTCCCTTTGC GTTCGCACCT CGAGCCCACC AACCATGCCA TCATTCAGAC    2940

GCTGCTCAAC TCCATGGCAC AGACGCGGC GCCGGCCTCC TGCTGTGTGC CAGCGCGCCT    3000

CAGCCCCATC AGCATCCTCT ACATCGACGC CGCCAACAAC GTTGTCTACA AGCAATACGA    3060

GGACATGGTG GTGGAGGCCT GCGGCTGCAG GTAGTCTAGA GTCGACCTGC AGTAATCGTA    3120

CAGGGTAGTA CAAATAAAAA AGGCACGTCA GATGACGTGC CTTTTTTCTT GTGAGCAGTA    3180

AGCTTGGCAC TGGCCGTCGT TTTACAACGT CGTGACTGGG AAAACCCTGG CGTTACCCAA    3240

CTTAATCGCC TTGCAGCACA TCCCCCTTTC GCCAGCTGGC GTAATAGCGA AGAGGCCCGC    3300

ACCGATCGCC CTTCCCAACA GTTGCGCAGC CTGAATGGCG AATGGCGCCT GATGCGGTAT    3360

TTTCTCCTTA CGCATCTGTG CGGTATTTCA CACCGCATAT ATGGTGCACT CTCAGTACAA    3420

TCTGCTCTGA TGCCGCATAG TTAAGCCAGC CCCGACACCC GCCAACACCC GCTGACGCGC    3480

CCTGACGGGC TTGTCTGCTC CCGGCATCCG CTTACAGACA AGCTGTGACC GTCTCCGGGA    3540

GCTGCATGTG TCAGAGGTTT TCACCGTCAT CACCGAAACG CGCGA                    3585

(2) INFORMATION FOR SEQ ID NO: 10:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: mouse (vii) IMMEDIATE SOURCE:
        (B) CLONE: mV1

(ix) FEATURE:
        (A) NAME/KEY: CDS
        (B) LOCATION: 28..243

(xi) SEQUENCE DESCRIPTION: SEQ ID NO: 10:

GGATCCAAGG AGCTCGGCTG GGACGAC TGG ATC ATC GCG CCA TTA GAC TAC          51
                            Trp Ile Ile Ala Pro Leu Asp Tyr
                              1               5

GAG GCA TAC CAC TGC GAG GGC GTT TGC GAC TTT CCT CTG CGC TCG CAC       99
Glu Ala Tyr His Cys Glu Gly Val Cys Asp Phe Pro Leu Arg Ser His
       10                  15                  20

CTG GAG CCT ACC AAC CAC GCC ATC ATT CAG ACG CTG CTC AAC TCC ATG      147
Leu Glu Pro Thr Asn His Ala Ile Ile Gln Thr Leu Leu Asn Ser Met
 25                  30                  35                  40

GCG CCC GAC GCT GCG CCA GCC TCC TGC TGC GTG CCC GCA AGG CTC AGT      195
Ala Pro Asp Ala Ala Pro Ala Ser Cys Cys Val Pro Ala Arg Leu Ser
                 45                  50                  55

CCC ATC AGC ATT CTC TAC ATC GAT GCC GCC AAC AAC GTG GTC TAC AAG      243
Pro Ile Ser Ile Leu Tyr Ile Asp Ala Ala Asn Asn Val Val Tyr Lys
                     60                  65                  70

CAATACGAGG ACATGGTGGT GGGGAATTC                                       272

(2) INFORMATION FOR SEQ ID NO: 11:
```

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO: 11:

Trp Ile Ile Ala Pro Leu Asp Tyr Glu Ala Tyr His Cys Glu Gly Val
 1               5                  10                  15

Cys Asp Phe Pro Leu Arg Ser His Leu Glu Pro Thr Asn His Ala Ile
            20                  25                  30

Ile Gln Thr Leu Leu Asn Ser Met Ala Pro Asp Ala Ala Pro Ala Ser
        35                  40                  45

Cys Cys Val Pro Ala Arg Leu Ser Pro Ile Ser Ile Leu Tyr Ile Asp
50                  55                  60

Ala Ala Asn Asn Val Val Tyr Lys
65                  70

(2) INFORMATION FOR SEQ ID NO: 12:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: mouse (vii) IMMEDIATE SOURCE:
        (B) CLONE: mV2

(ix) FEATURE:
        (A) NAME/KEY: CDS
        (B) LOCATION: 28..243

(xi) SEQUENCE DESCRIPTION: SEQ ID NO: 12:

GGATCCAAGG AGCTCGGCTG GGACGAC TGG ATT ATC GCG CCC CTA GAG TAC         51
                              Trp Ile Ile Ala Pro Leu Glu Tyr
                               1               5

GAG GCC TAT CAC TGC GAG GGC GTG TGC GAC TTT CCG CTG CGC TCG CAC       99
Glu Ala Tyr His Cys Glu Gly Val Cys Asp Phe Pro Leu Arg Ser His
         10                  15                  20

CTT GAG CCC ACT AAC CAT GCC ATC ATT CAG ACG CTG ATG AAC TCC ATG      147
Leu Glu Pro Thr Asn His Ala Ile Ile Gln Thr Leu Met Asn Ser Met
 25                  30                  35                  40

GAC CCG GGC TCC ACC CCG CCT AGC TGC TGC GTT CCC ACC AAA CTG ACT      195
Asp Pro Gly Ser Thr Pro Pro Ser Cys Cys Val Pro Thr Lys Leu Thr
                 45                  50                  55

CCC ATT AGC ATC CTG TAC ATC GAC GCG GGC AAT AAT GTA GTC TAC AAG      243
Pro Ile Ser Ile Leu Tyr Ile Asp Ala Gly Asn Asn Val Val Tyr Lys
             60                  65                  70

CAATACGAGG ACATGGTGGT GGGGAATTC                                      272

(2) INFORMATION FOR SEQ ID NO: 13:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO: 13:

Trp Ile Ile Ala Pro Leu Glu Tyr Glu Ala Tyr His Cys Glu Gly Val
1               5                   10                  15

Cys Asp Phe Pro Leu Arg Ser His Leu Glu Pro Thr Asn His Ala Ile
                20                  25                  30

Ile Gln Thr Leu Met Asn Ser Met Asp Pro Gly Ser Thr Pro Pro Ser
        35                  40                  45

Cys Cys Val Pro Thr Lys Leu Thr Pro Ile Ser Ile Leu Tyr Ile Asp
50                  55                  60

Ala Gly Asn Asn Val Val Tyr Lys
65                  70

(2) INFORMATION FOR SEQ ID NO: 14:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: mouse (vii) IMMEDIATE SOURCE:
        (B) CLONE: mV9

(ix) FEATURE:
        (A) NAME/KEY: CDS
        (B) LOCATION: 28..243

(xi) SEQUENCE DESCRIPTION: SEQ ID NO: 14:

```
GGATCCAAGG AGCTCGGCTG GGACGAC TGG ATC ATC GCA CCT CTT GAG TAT        51
                                Trp Ile Ile Ala Pro Leu Glu Tyr
                                 1               5

GAG GCC TTC CAC TGC GAA GGA CTG TGT GAG TTC CCC TTG CGC TCC CAC      99
Glu Ala Phe His Cys Glu Gly Leu Cys Glu Phe Pro Leu Arg Ser His
    10                  15                  20

TTG GAG CCC ACA AAC CAC GCA GTC ATT CAG ACC CTA ATG AAC TCT ATG     147
Leu Glu Pro Thr Asn His Ala Val Ile Gln Thr Leu Met Asn Ser Met
25                  30                  35                  40

GAC CCT GAA TCC ACA CCA CCC ACT TGT TGT GTG CCT ACA CGG CTG AGT     195
Asp Pro Glu Ser Thr Pro Pro Thr Cys Cys Val Pro Thr Arg Leu Ser
                45                  50                  55

CCT ATT AGC ATC CTC TTC ATC GAC TCT GCC AAC AAC GTG GTG TAT AAA     243
Pro Ile Ser Ile Leu Phe Ile Asp Ser Ala Asn Asn Val Val Tyr Lys
                60                  65                  70

CAATACGAGG ACATGGTGGT GGGGAATTC                                     272
```

(2) INFORMATION FOR SEQ ID NO: 15:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO: 15:

Trp Ile Ile Ala Pro Leu Glu Tyr Glu Ala Phe His Cys Glu Gly Leu
1               5                   10                  15

Cys Glu Phe Pro Leu Arg Ser His Leu Glu Pro Thr Asn His Ala Val

-continued

```
                 20                  25                  30
Ile Gln Thr Leu Met Asn Ser Met Asp Pro Glu Ser Thr Pro Pro Thr
             35                  40                  45
Cys Cys Val Pro Thr Arg Leu Ser Pro Ile Ser Ile Leu Phe Ile Asp
         50                  55                  60
Ser Ala Asn Asn Val Val Tyr Lys
 65                  70
```

(2) INFORMATION FOR SEQ ID NO: 16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: BMP/TGF-beta consensus sequence (xi) SEQUENCE DESCRIPTION: SEQ ID NO: 16:

```
Trp Xaa Asp Trp Ile Xaa Ala
 1               5
```

(2) INFORMATION FOR SEQ ID NO: 17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: oligonucleotide #1

(xi) SEQUENCE DESCRIPTION: SEQ ID NO: 17:

```
CGGATCCTGG VANGAYTGGA THRTNGC                                27
```

(2) INFORMATION FOR SEQ ID NO: 18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: BMP/TGF-beta consensus sequence (xi) SEQUENCE DESCRIPTION: SEQ ID NO: 18:

```
His Ala Ile Xaa Gln Thr
 1               5
```

(2) INFORMATION FOR SEQ ID NO: 19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:

(B) CLONE: oligonucleotide #2

(xi) SEQUENCE DESCRIPTION: SEQ ID NO: 19:

TTTCTAGAAR NGTYTGNACD ATNGCRTG                                      28

(2) INFORMATION FOR SEQ ID NO: 20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: oligonucleotide #3

(xi) SEQUENCE DESCRIPTION: SEQ ID NO: 20:

CCACTGCGAG GGCCTTTGCG ACTTCCCTTT GCGTTCGCAC                          40

(2) INFORMATION FOR SEQ ID NO: 21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (A) LIBRARY: oligonucleotide #4

(xi) SEQUENCE DESCRIPTION: SEQ ID NO: 21:

TGCGGATCCA GCCGCTGCAG CCGCAAGCC                                      29

(2) INFORMATION FOR SEQ ID NO: 22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: oligonucleotide #5

(xi) SEQUENCE DESCRIPTION: SEQ ID NO: 22:

GACTCTAGAC TACCTGCAGC CGCAGGCCT                                      29

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (A) LIBRARY: oligonucleotide #6

(xi) SEQUENCE DESCRIPTION: SEQ ID NO: 23:

GCGGATCCAA GGAGCTCGGC TGGGACGA                                       28

(2) INFORMATION FOR SEQ ID NO: 24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: oligonucleotide #7

(xi) SEQUENCE DESCRIPTION: SEQ ID NO: 24:

```
GGAATTCCCC ACCACCATGT CCTCGTAT                                28
```

(2) INFORMATION FOR SEQ ID NO: 25:

(i) SEQUENCE CHARACTERISTICS:
        (A) LENGTH: 1171 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Human VL-1 protein (ix) FEATURE:
        (A) NAME/KEY: CDS
        (B) LOCATION: 2..964

(ix) FEATURE:
        (A) NAME/KEY: mat_peptide
        (B) LOCATION: 605..964

(xi) SEQUENCE DESCRIPTION: SEQ ID NO: 25:

```
G AAT TCG GAT CTC TCG CAC ACT CCT CTC CGG AGA CAG AAG TAT TTG        46
  Asn Ser Asp Leu Ser His Thr Pro Leu Arg Arg Gln Lys Tyr Leu
  -201-200            -195                -190

TTT GAT GTG TCC ATG CTC TCA GAC AAA GAA GAG CTG GTG GGC GCG GAG      94
Phe Asp Val Ser Met Leu Ser Asp Lys Glu Glu Leu Val Gly Ala Glu
       -185               -180                -175

CTG CGG CTC TTT CGC CAG GCG CCC TCA GCG CCC TGG GGG CCA CCA GCC     142
Leu Arg Leu Phe Arg Gln Ala Pro Ser Ala Pro Trp Gly Pro Pro Ala
-170                -165                -160                -155

GGG CCG CTC CAC GTG CAG CTC TTC CCT TGC CTT TCG CCC CTA CTG CTG     190
Gly Pro Leu His Val Gln Leu Phe Pro Cys Leu Ser Pro Leu Leu Leu
                -150                -145                -140

GAC GCG CGG ACC CTG GAC CCG CAG GGG GCG CCG CCG GCC GGC TGG GAA     238
Asp Ala Arg Thr Leu Asp Pro Gln Gly Ala Pro Pro Ala Gly Trp Glu
        -135                -130                -125

GTC TTC GAC GTG TGG CAG GGC CTG CGC CAC CAG CCC TGG AAG CAG CTG     286
Val Phe Asp Val Trp Gln Gly Leu Arg His Gln Pro Trp Lys Gln Leu
        -120                -115                -110

TGC TTG GAG CTG CGG GCC GCA TGG GGC GAG CTG GAC GCC GGG GAG GCC     334
Cys Leu Glu Leu Arg Ala Ala Trp Gly Glu Leu Asp Ala Gly Glu Ala
        -105                -100                -95

GAG GCG CGC GCG CGG GGA CCC CAG CAA CCG CCG CCC CCG GAC CTG CGG     382
Glu Ala Arg Ala Arg Gly Pro Gln Gln Pro Pro Pro Pro Asp Leu Arg
-90                 -85                 -80                 -75

AGT CTG GGC TTC GGC CGG AGG GTG CGG CCT CCC CAG GAG CGG GCC CTG     430
Ser Leu Gly Phe Gly Arg Arg Val Arg Pro Pro Gln Glu Arg Ala Leu
                -70                 -65                 -60

CTG GTG GTA TTC ACC AGA TCC CAG CGC AAG AAC CTG TTC GCA GAG ATG     478
Leu Val Val Phe Thr Arg Ser Gln Arg Lys Asn Leu Phe Ala Glu Met
```

```
                    -55                 -50                 -45
CGC GAG CAG CTG GGC TCG GCC GAG GCT GCG GGC CCG GGC GCG GGC GCC      526
Arg Glu Gln Leu Gly Ser Ala Glu Ala Ala Gly Pro Gly Ala Gly Ala
            -40                 -35                 -30

GAG GGG TCG TGG CCG CCG CCG TCG GGC GCC CCG GAT GCC AGG CCT TGG      574
Glu Gly Ser Trp Pro Pro Pro Ser Gly Ala Pro Asp Ala Arg Pro Trp
        -25                 -20                 -15

CTG CCC TCG CCC GGC CGC CGG CGG CGG CGC ACG GCC TTC GCC AGT CGC      622
Leu Pro Ser Pro Gly Arg Arg Arg Arg Arg Thr Ala Phe Ala Ser Arg
-10                  -5                   1                  5

CAT GGC AAG CGG CAC GGC AAG AAG TCC AGG CTA CGC TGC AGC AAG AAG      670
His Gly Lys Arg His Gly Lys Lys Ser Arg Leu Arg Cys Ser Lys Lys
            10                  15                  20

CCC CTG CAC GTG AAC TTC AAG GAG CTG GGC TGG GAC GAC TGG ATT ATC      718
Pro Leu His Val Asn Phe Lys Glu Leu Gly Trp Asp Asp Trp Ile Ile
        25                  30                  35

GCG CCC CTG GAG TAC GAG GCC TAT CAC TGC GAG GGT GTA TGC GAC TTC      766
Ala Pro Leu Glu Tyr Glu Ala Tyr His Cys Glu Gly Val Cys Asp Phe
    40                  45                  50

CCG CTG CGC TCG CAC CTG GAG CCC ACC AAC CAC GCC ATC ATC CAG ACG      814
Pro Leu Arg Ser His Leu Glu Pro Thr Asn His Ala Ile Ile Gln Thr
55                  60                  65                  70

CTG ATG AAC TCC ATG GAC CCC GGC TCC ACC CCG CCC AGC TGC TGC GTG      862
Leu Met Asn Ser Met Asp Pro Gly Ser Thr Pro Pro Ser Cys Cys Val
            75                  80                  85

CCC ACC AAA TTG ACT CCC ATC AGC ATT CTA TAC ATC GAC GCG GGC AAT      910
Pro Thr Lys Leu Thr Pro Ile Ser Ile Leu Tyr Ile Asp Ala Gly Asn
        90                  95                  100

AAT GTG GTC TAC AAG CAG TAC GAG GAC ATG GTG GTG GAG TCG TGC GGC      958
Asn Val Val Tyr Lys Gln Tyr Glu Asp Met Val Val Glu Ser Cys Gly
    105                 110                 115

TGC AGG TAGCGGTGCC TTTCCCGCCG CCTTGGCCCG GAACCAAGGT GGGCCAAGGT      1014
Cys Arg
    120

CCGCCTTGCA GGGGAGGCCT GGCTGCAGAG AGGCGGAGGA GGAAGCTGGC GCTGGGGAG    1074

GCTGAGGGTG AGGGAACAGC CTGGATGTGA GAGCCGGTGG GAGAGAAGGG AGCGCACCTT   1134

CCCAGTAACT TCTACCTGCC AGCCCAGAGG GAAATAT                            1171

(2) INFORMATION FOR SEQ ID NO: 26:

(i) SEQUENCE CHARACTERISTICS:
        (A) LENGTH: 321 amino acids
        (B) TYPE: amino acid
        (D) TOPOLOGY: linear (ii) MOLECULE TYPE: protein (xi) SEQUENCE DESCRIPTION: SEQ ID NO: 26:

Asn Ser Asp Leu Ser His Thr Pro Leu Arg Arg Gln Lys Tyr Leu Phe
-201 -200                -195                -190

Asp Val Ser Met Leu Ser Asp Lys Glu Glu Leu Val Gly Ala Glu Leu
-185                 -180                -175                -170

Arg Leu Phe Arg Gln Ala Pro Ser Ala Pro Trp Gly Pro Pro Ala Gly
            -165                -160                -155

Pro Leu His Val Gln Leu Phe Pro Cys Leu Ser Pro Leu Leu Leu Asp
            -150                -145                -140

Ala Arg Thr Leu Asp Pro Gln Gly Ala Pro Pro Ala Gly Trp Glu Val
        -135                -130                -125
```

-continued

```
Phe Asp Val Trp Gln Gly Leu Arg His Gln Pro Trp Lys Gln Leu Cys
    -120                -115                -110
Leu Glu Leu Arg Ala Ala Trp Gly Glu Leu Asp Ala Gly Glu Ala Glu
-105                -100                -95                 -90
Ala Arg Ala Arg Gly Pro Gln Gln Pro Pro Pro Asp Leu Arg Ser
                 -85                 -80                 -75
Leu Gly Phe Gly Arg Arg Val Arg Pro Pro Gln Glu Arg Ala Leu Leu
             -70                 -65                 -60
Val Val Phe Thr Arg Ser Gln Arg Lys Asn Leu Phe Ala Glu Met Arg
         -55                 -50                 -45
Glu Gln Leu Gly Ser Ala Glu Ala Ala Gly Pro Gly Ala Gly Ala Glu
    -40                 -35                 -30
Gly Ser Trp Pro Pro Pro Ser Gly Ala Pro Asp Ala Arg Pro Trp Leu
-25                 -20                 -15                 -10
Pro Ser Pro Gly Arg Arg Arg Arg Thr Ala Phe Ala Ser Arg His
                 -5                   1                   5
Gly Lys Arg His Gly Lys Lys Ser Arg Leu Arg Cys Ser Lys Lys Pro
             10                  15                  20
Leu His Val Asn Phe Lys Glu Leu Gly Trp Asp Asp Trp Ile Ile Ala
         25                  30                  35
Pro Leu Glu Tyr Glu Ala Tyr His Cys Glu Gly Val Cys Asp Phe Pro
40                  45                  50                  55
Leu Arg Ser His Leu Glu Pro Thr Asn His Ala Ile Ile Gln Thr Leu
             60                  65                  70
Met Asn Ser Met Asp Pro Gly Ser Thr Pro Pro Ser Cys Cys Val Pro
             75                  80                  85
Thr Lys Leu Thr Pro Ile Ser Ile Leu Tyr Ile Asp Ala Gly Asn Asn
             90                  95                 100
Val Val Tyr Lys Gln Tyr Glu Asp Met Val Val Glu Ser Cys Gly Cys
         105                 110                 115
Arg
120
```

(2) INFORMATION FOR SEQ ID NO: 27:

(i) SEQUENCE CHARACTERISTICS:
        (A) LENGTH: 1233 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: DNA encoding BMP2 propeptide/BMP-12 mature
            peptide (ix) FEATURE:
        (A) NAME/KEY: CDS
        (B) LOCATION: 1..1233

(ix) FEATURE:
        (A) NAME/KEY: mat_peptide
        (B) LOCATION: 847..1233

(xi) SEQUENCE DESCRIPTION: SEQ ID NO: 27:

```
ATG GTG GCC GGG ACC CGC TGT CTT CTA GCG TTG CTG CTT CCC CAG GTC        48
Met Val Ala Gly Thr Arg Cys Leu Leu Ala Leu Leu Leu Pro Gln Val
-282        -280                -275                -270

CTC CTG GGC GGC GCG GCT GGC CTC GTT CCG GAG CTG GGC CGC AGG AAG        96
```

-continued

```
Leu Leu Gly Gly Ala Ala Gly Leu Val Pro Glu Leu Gly Arg Arg Lys
    -265              -260              -255

TTC GCG GCG GCG TCG TCG GGC CGC CCC TCA TCC CAG CCC TCT GAC GAG          144
Phe Ala Ala Ala Ser Ser Gly Arg Pro Ser Ser Gln Pro Ser Asp Glu
-250              -245              -240              -235

GTC CTG AGC GAG TTC GAG TTG CGG CTG CTC AGC ATG TTC GGC CTG AAA          192
Val Leu Ser Glu Phe Glu Leu Arg Leu Leu Ser Met Phe Gly Leu Lys
              -230              -225              -220

CAG AGA CCC ACC CCC AGC AGG GAC GCC GTG GTG CCC CCC TAC ATG CTA          240
Gln Arg Pro Thr Pro Ser Arg Asp Ala Val Val Pro Pro Tyr Met Leu
        -215              -210              -205

GAC CTG TAT CGC AGG CAC TCA GGT CAG CCG GGC TCA CCC GCC CCA GAC          288
Asp Leu Tyr Arg Arg His Ser Gly Gln Pro Gly Ser Pro Ala Pro Asp
        -200              -195              -190

CAC CGG TTG GAG AGG GCA GCC AGC CGA GCC AAC ACT GTG CGC AGC TTC          336
His Arg Leu Glu Arg Ala Ala Ser Arg Ala Asn Thr Val Arg Ser Phe
        -185              -180              -175

CAC CAT GAA GAA TCT TTG GAA GAA CTA CCA GAA ACG AGT GGG AAA ACA          384
His His Glu Glu Ser Leu Glu Glu Leu Pro Glu Thr Ser Gly Lys Thr
-170              -165              -160              -155

ACC CGG AGA TTC TTC TTT AAT TTA AGT TCT ATC CCC ACG GAG GAG TTT          432
Thr Arg Arg Phe Phe Phe Asn Leu Ser Ser Ile Pro Thr Glu Glu Phe
              -150              -145              -140

ATC ACC TCA GCA GAG CTT CAG GTT TTC CGA GAA CAG ATG CAA GAT GCT          480
Ile Thr Ser Ala Glu Leu Gln Val Phe Arg Glu Gln Met Gln Asp Ala
        -135              -130              -125

TTA GGA AAC AAT AGC AGT TTC CAT CAC CGA ATT AAT ATT TAT GAA ATC          528
Leu Gly Asn Asn Ser Ser Phe His His Arg Ile Asn Ile Tyr Glu Ile
        -120              -115              -110

ATA AAA CCT GCA ACA GCC AAC TCG AAA TTC CCC GTG ACC AGA CTT TTG          576
Ile Lys Pro Ala Thr Ala Asn Ser Lys Phe Pro Val Thr Arg Leu Leu
-105              -100              -95

GAC ACC AGG TTG GTG AAT CAG AAT GCA AGC AGG TGG GAA AGT TTT GAT          624
Asp Thr Arg Leu Val Asn Gln Asn Ala Ser Arg Trp Glu Ser Phe Asp
-90              -85              -80              -75

GTC ACC CCC GCT GTG ATG CGG TGG ACT GCA CAG GGA CAC GCC AAC CAT          672
Val Thr Pro Ala Val Met Arg Trp Thr Ala Gln Gly His Ala Asn His
              -70              -65              -60

GGA TTC GTG GTG GAA GTG GCC CAC TTG GAG GAG AAA CAA GGT GTC TCC          720
Gly Phe Val Val Glu Val Ala His Leu Glu Glu Lys Gln Gly Val Ser
        -55              -50              -45

AAG AGA CAT GTT AGG ATA AGC AGG TCT TTG CAC CAA GAT GAA CAC AGC          768
Lys Arg His Val Arg Ile Ser Arg Ser Leu His Gln Asp Glu His Ser
        -40              -35              -30

TGG TCA CAG ATA AGG CCA TTG CTA GTA ACT TTT GGC CAT GAT GGA AAA          816
Trp Ser Gln Ile Arg Pro Leu Leu Val Thr Phe Gly His Asp Gly Lys
-25              -20              -15

GGG CAT CCT CTC CAC AAA AGA GAA AAA CGT ACG GCG TTG GCC GGG ACG          864
Gly His Pro Leu His Lys Arg Glu Lys Arg Thr Ala Leu Ala Gly Thr
-10              -5                1                5

CGG ACA GCG CAG GGC AGC GGC GGG GGC GCG GGC CGG GGC CAC GGG CGC          912
Arg Thr Ala Gln Gly Ser Gly Gly Gly Ala Gly Arg Gly His Gly Arg
              10               15               20

AGG GGC CGG AGC CGC TGC AGC CGC AAG CCG TTG CAC GTG GAC TTC AAG          960
Arg Gly Arg Ser Arg Cys Ser Arg Lys Pro Leu His Val Asp Phe Lys
        25               30               35

GAG CTC GGC TGG GAC GAC TGG ATC ATC GCG CCG CTG GAC TAC GAG GCG         1008
Glu Leu Gly Trp Asp Asp Trp Ile Ile Ala Pro Leu Asp Tyr Glu Ala
        40               45               50
```

```
TAC CAC TGC GAG GGC CTT TGC GAC TTC CCT TTG CGT TCG CAC CTC GAG      1056
Tyr His Cys Glu Gly Leu Cys Asp Phe Pro Leu Arg Ser His Leu Glu
 55              60                  65                  70

CCC ACC AAC CAT GCC ATC ATT CAG ACG CTG CTC AAC TCC ATG GCA CCA      1104
Pro Thr Asn His Ala Ile Ile Gln Thr Leu Leu Asn Ser Met Ala Pro
             75                  80                  85

GAC GCG GCG CCG GCC TCC TGC TGT GTG CCA GCG CGC CTC AGC CCC ATC      1152
Asp Ala Ala Pro Ala Ser Cys Cys Val Pro Ala Arg Leu Ser Pro Ile
         90                  95                 100

AGC ATC CTC TAC ATC GAC GCC GCC AAC AAC GTT GTC TAC AAG CAA TAC      1200
Ser Ile Leu Tyr Ile Asp Ala Ala Asn Asn Val Val Tyr Lys Gln Tyr
            105                 110                 115

GAG GAC ATG GTG GTG GAG GCC TGC GGC TGC AGG                          1233
Glu Asp Met Val Val Glu Ala Cys Gly Cys Arg
        120                 125
```

(2) INFORMATION FOR SEQ ID NO: 28:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO: 28:

```
Met Val Ala Gly Thr Arg Cys Leu Leu Ala Leu Leu Leu Pro Gln Val
-282    -280                -275                -270

Leu Leu Gly Gly Ala Ala Gly Leu Val Pro Glu Leu Gly Arg Arg Lys
        -265                -260            -255

Phe Ala Ala Ala Ser Ser Gly Arg Pro Ser Ser Gln Pro Ser Asp Glu
-250                -245                -240                -235

Val Leu Ser Glu Phe Glu Leu Arg Leu Leu Ser Met Phe Gly Leu Lys
            -230                -225                -220

Gln Arg Pro Thr Pro Ser Arg Asp Ala Val Val Pro Pro Tyr Met Leu
            -215                -210                -205

Asp Leu Tyr Arg Arg His Ser Gly Gln Pro Gly Ser Pro Ala Pro Asp
        -200                -195                -190

His Arg Leu Glu Arg Ala Ala Ser Arg Ala Asn Thr Val Arg Ser Phe
    -185                -180                -175

His His Glu Glu Ser Leu Glu Glu Leu Pro Glu Thr Ser Gly Lys Thr
-170                -165                -160                -155

Thr Arg Arg Phe Phe Phe Asn Leu Ser Ser Ile Pro Thr Glu Glu Phe
                -150                -145                -140

Ile Thr Ser Ala Glu Leu Gln Val Phe Arg Glu Gln Met Gln Asp Ala
            -135                -130                -125

Leu Gly Asn Asn Ser Ser Phe His His Arg Ile Asn Ile Tyr Glu Ile
        -120                -115                -110

Ile Lys Pro Ala Thr Ala Asn Ser Lys Phe Pro Val Thr Arg Leu Leu
        -105                -100                -95

Asp Thr Arg Leu Val Asn Gln Asn Ala Ser Arg Trp Glu Ser Phe Asp
-90                 -85                 -80                 -75

Val Thr Pro Ala Val Met Arg Trp Thr Ala Gln Gly His Ala Asn His
                -70                 -65                 -60

Gly Phe Val Val Glu Val Ala His Leu Glu Glu Lys Gln Gly Val Ser
                -55                 -50                 -45

Lys Arg His Val Arg Ile Ser Arg Ser Leu His Gln Asp Glu His Ser
        -40                 -35                 -30
```

```
Trp Ser Gln Ile Arg Pro Leu Leu Val Thr Phe Gly His Asp Gly Lys
    -25             -20                 -15

Gly His Pro Leu His Lys Arg Glu Lys Arg Thr Ala Leu Ala Gly Thr
-10              -5                   1                   5

Arg Thr Ala Gln Gly Ser Gly Gly Ala Gly Arg Gly His Gly Arg
            10              15                  20

Arg Gly Arg Ser Arg Cys Ser Arg Lys Pro Leu His Val Asp Phe Lys
        25              30                  35

Glu Leu Gly Trp Asp Asp Trp Ile Ile Ala Pro Leu Asp Tyr Glu Ala
        40              45                  50

Tyr His Cys Glu Gly Leu Cys Asp Phe Pro Leu Arg Ser His Leu Glu
55              60                  65                      70

Pro Thr Asn His Ala Ile Ile Gln Thr Leu Leu Asn Ser Met Ala Pro
                75              80                  85

Asp Ala Ala Pro Ala Ser Cys Cys Val Pro Ala Arg Leu Ser Pro Ile
            90                  95                  100

Ser Ile Leu Tyr Ile Asp Ala Ala Asn Asn Val Val Tyr Lys Gln Tyr
        105                 110                 115

Glu Asp Met Val Val Glu Ala Cys Gly Cys Arg
    120                 125
```

(2) INFORMATION FOR SEQ ID NO: 29:

(i) SEQUENCE CHARACTERISTICS:
        (A) LENGTH: 1203 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: murine MV1

(ix) FEATURE:
        (A) NAME/KEY: CDS
        (B) LOCATION: 2..721

(xi) SEQUENCE DESCRIPTION: SEQ ID NO: 29:

```
A AAG TTC TGC CTG GTG CTG GNG NCG GTG ACG GCC TCG GAG AGC AGN      46
  Lys Phe Cys Leu Val Leu Xaa Xaa Val Thr Ala Ser Glu Ser Xaa
   1               5                  10                  15

CNG CTG GCC CTG AGA CGA CTG GGC TTC GGC TGN CCG GGC GGT GGC GAC    94
Xaa Leu Ala Leu Arg Arg Leu Gly Phe Gly Xaa Pro Gly Gly Gly Asp
                20                  25                  30

GGC GGC GGC ACT GCG GNC GAG GAG CGC GCG CTG TTG GTG ATC TCC TCC    142
Gly Gly Gly Thr Ala Xaa Glu Glu Arg Ala Leu Leu Val Ile Ser Ser
            35                  40                  45

CGT ACG CAA AGG AAA GAG AGT CTG TTC CGG GAG ATC CGA GCC CAG GCC    190
Arg Thr Gln Arg Lys Glu Ser Leu Phe Arg Glu Ile Arg Ala Gln Ala
        50                  55                  60

CGT GCT CTC CGG GCC GCT GCA GAG CCG CCA CCG GAT CCA GGA CCA GGC    238
Arg Ala Leu Arg Ala Ala Ala Glu Pro Pro Pro Asp Pro Gly Pro Gly
65                  70                  75

GCT GGG TCA CGC AAA GCC AAC CTG GGC GGT CGC AGG CGG CAG CGG ACT    286
Ala Gly Ser Arg Lys Ala Asn Leu Gly Gly Arg Arg Arg Gln Arg Thr
80                  85                  90                  95

GCG CTG GCT GGG ACT CGG GGA GNG NAG GGA AGC GGT GGT GGC GGC GGT    334
Ala Leu Ala Gly Thr Arg Gly Xaa Xaa Gly Ser Gly Gly Gly Gly Gly
                100                 105                 110
```

```
GGC GGT GGC GGC GGC GGC GGC GGC GGC GGC GGC GGC GGC GGC GCA        382
Gly Gly Gly Gly Gly Gly Gly Gly Gly Gly Gly Gly Gly Gly Ala
        115                 120                 125

GGC AGG GGC CAC GGG CGC AGA GGC CGG AGC CGC TGC GGT CGC AAG TCA    430
Gly Arg Gly His Gly Arg Arg Gly Arg Ser Arg Cys Gly Arg Lys Ser
        130                 135                 140

CTG CAC GTG GAC TTT AAG GAG CTG GGC TGG GAC GAC TGG ATC ATC GCG    478
Leu His Val Asp Phe Lys Glu Leu Gly Trp Asp Asp Trp Ile Ile Ala
145                 150                 155

CCA TTA GAC TAC GAG GCA TAC CAC TGC GAG GGC GTT TGC GAC TTT CCT    526
Pro Leu Asp Tyr Glu Ala Tyr His Cys Glu Gly Val Cys Asp Phe Pro
160                 165                 170                 175

CTG CGC TCG CAC CTG GAG CCT ACC AAC CAC GCC ATC ATT CAG ACG CTG    574
Leu Arg Ser His Leu Glu Pro Thr Asn His Ala Ile Ile Gln Thr Leu
                180                 185                 190

CTC AAC TCC ATG GCG CCC GAC GCT GCG CCA GCC TCC TGC TGC GTG CCC    622
Leu Asn Ser Met Ala Pro Asp Ala Ala Pro Ala Ser Cys Cys Val Pro
                195                 200                 205

GCA AGG CTC AGT CCC ATC AGC ATT CTC TAC ATC GAT GCC GCC AAC AAC    670
Ala Arg Leu Ser Pro Ile Ser Ile Leu Tyr Ile Asp Ala Ala Asn Asn
                210                 215                 220

GTG GTC TAC AAG CAG TAC GAA GAC ATG GTG GTG GAG GCC TGC GGC TGC    718
Val Val Tyr Lys Gln Tyr Glu Asp Met Val Val Glu Ala Cys Gly Cys
225                 230                 235

AGG TAGCATGCGG TCTGGGGAGG GTCTGGCCGC CCAGGACCCT AGCTCAAGAG          771
Arg
240

CAGGTGTCAT CAGGCCCGAG GGACGGCGGA CTATGGCCTC TGCCAGCACA GAGGAGAGCA   831

CACAGTTAAC ACTCACATTT ACACACTCCT TCACTCACGC ACATGTTTAC CGTGGACGGC   891

AGGCGCTAAA AGCCTTGCTT ATTTGCTACC ATTGATACAA ACCTCTGTCC TTTTCGGGAG   951

AGGGAAGGGC ATCTGTGTTT ATGTTGCAGT AATTGGCACT AAATCCAAGT AGAAATGGGT  1011

TAGCATTGGA TTCTCCTTTT AGTTGGAGGC GGTGTGGCTG GATTCCTGAC GTTGGATATG  1071

GAGTGCACTG CAGGGCTGGG ATACCCAGAT TCTCTGGAGT GGGCATTGGG AACCTTCAAA  1131

AGTAAGGAGC CACTGGGGCT TGGGAGGGAG CACCCGGTTC CTAAACAAGT CTGATGTGTA  1191

CTGCTCAGTT TG                                                     1203

(2) INFORMATION FOR SEQ ID NO: 30:

(i) SEQUENCE CHARACTERISTICS:
        (A) LENGTH: 240 amino acids
        (B) TYPE: amino acid
        (D) TOPOLOGY: linear (ii) MOLECULE TYPE: protein (xi) SEQUENCE DESCRIPTION: SEQ ID NO: 30:

Lys Phe Cys Leu Val Leu Xaa Xaa Val Thr Ala Ser Glu Ser Xaa Xaa
1               5                   10                  15

Leu Ala Leu Arg Arg Leu Gly Phe Gly Xaa Pro Gly Gly Gly Asp Gly
            20                  25                  30

Gly Gly Thr Ala Xaa Glu Glu Arg Ala Leu Leu Val Ile Ser Ser Arg
        35                  40                  45

Thr Gln Arg Lys Glu Ser Leu Phe Arg Glu Ile Arg Ala Gln Ala Arg
    50                  55                  60

Ala Leu Arg Ala Ala Ala Glu Pro Pro Asp Pro Gly Pro Gly Ala
65                  70                  75                  80
```

```
Gly Ser Arg Lys Ala Asn Leu Gly Gly Arg Arg Gln Arg Thr Ala
             85                  90                  95

Leu Ala Gly Thr Arg Gly Xaa Xaa Gly Ser Gly Gly Gly Gly Gly
            100                 105                 110

Gly Gly Gly Gly Gly Gly Gly Gly Gly Gly Gly Gly Gly Ala Gly
            115                 120                 125

Arg Gly His Gly Arg Arg Gly Arg Ser Arg Cys Gly Arg Lys Ser Leu
        130                 135                 140

His Val Asp Phe Lys Glu Leu Gly Trp Asp Asp Trp Ile Ile Ala Pro
145                 150                 155                 160

Leu Asp Tyr Glu Ala Tyr His Cys Glu Gly Val Cys Asp Phe Pro Leu
                165                 170                 175

Arg Ser His Leu Glu Pro Thr Asn His Ala Ile Ile Gln Thr Leu Leu
            180                 185                 190

Asn Ser Met Ala Pro Asp Ala Ala Pro Ala Ser Cys Cys Val Pro Ala
        195                 200                 205

Arg Leu Ser Pro Ile Ser Ile Leu Tyr Ile Asp Ala Ala Asn Asn Val
    210                 215                 220

Val Tyr Lys Gln Tyr Glu Asp Met Val Val Glu Ala Cys Gly Cys Arg
225                 230                 235                 240

(2) INFORMATION FOR SEQ ID NO: 31:

(i) SEQUENCE CHARACTERISTICS:
        (A) LENGTH: 1046 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: MURINE MV2

(ix) FEATURE:
         (A) NAME/KEY: CDS
         (B) LOCATION: 2..790

(xi) SEQUENCE DESCRIPTION: SEQ ID NO: 31:

A AGA AAA CAA GCT TGC ATT CCT GCA GGT CCG ACT CTA AGA GGA TCC         46
  Arg Lys Gln Ala Cys Ile Pro Ala Gly Pro Thr Leu Arg Gly Ser
   1               5                  10                  15

TCA GGG ACC CAA CCC AGG CCG GCT GGG AAG TCT TTC GAC GTG TGG CAG       94
Ser Gly Thr Gln Pro Arg Pro Ala Gly Lys Ser Phe Asp Val Trp Gln
             20                  25                  30

GGC CTG CGC CCT CAG CCT TGG AAG CAG CTG TGC CTG GAG TTG CGG GCA      142
Gly Leu Arg Pro Gln Pro Trp Lys Gln Leu Cys Leu Glu Leu Arg Ala
         35                  40                  45

GCC TGG GGT GAG CTG GAC RCC GGG GAT ACG GGG GCG CGC GCG AGG GGT      190
Ala Trp Gly Glu Leu Asp Xaa Gly Asp Thr Gly Ala Arg Ala Arg Gly
     50                  55                  60

CCC CAG CAG CCA CCG CCT CTG GAC CTG CGG AGT CTG GGC TTC GGT CGG      238
Pro Gln Gln Pro Pro Pro Leu Asp Leu Arg Ser Leu Gly Phe Gly Arg
 65                  70                  75

AGG GTG AGA CCG CCC CAG GAG CGC GCC CTG CTT GTA GTG TTC ACC AGA      286
Arg Val Arg Pro Pro Gln Glu Arg Ala Leu Leu Val Val Phe Thr Arg
 80                  85                  90                  95

TCG CAG CGC AAG AAC CTG TTC ACT GAG ATG CAT GAG CAG CTG GGC TCT      334
```

```
Ser Gln Arg Lys Asn Leu Phe Thr Glu Met His Glu Gln Leu Gly Ser
                100                 105                 110

GCA GAG GCT GCG GGA GCC GAG GGG TCA TGT CCA GCG CCG TCG GGC TCC      382
Ala Glu Ala Ala Gly Ala Glu Gly Ser Cys Pro Ala Pro Ser Gly Ser
            115                 120                 125

CCA GAC ACC GGG TCT TGG CTG CCC TCG CCC GGC CGC GGG CGG CGA CGC      430
Pro Asp Thr Gly Ser Trp Leu Pro Ser Pro Gly Arg Arg Arg Arg Arg
        130                 135                 140

ACC GCC TTC GCC AGC CGT CAC GGC AAG CGA CAT GGC AAG AAG TCC AGG      478
Thr Ala Phe Ala Ser Arg His Gly Lys Arg His Gly Lys Lys Ser Arg
    145                 150                 155

CTG CGC TGC AGC AGA AAG CCT CTG CAC GTG AAT TTT AAG GAG TTA GGC      526
Leu Arg Cys Ser Arg Lys Pro Leu His Val Asn Phe Lys Glu Leu Gly
160                 165                 170                 175

TGG GAC GAC TGG ATT ATC GCG CCC CTA GAG TAC GAG GCC TAT CAC TGC      574
Trp Asp Asp Trp Ile Ile Ala Pro Leu Glu Tyr Glu Ala Tyr His Cys
                180                 185                 190

GAG GGC GTG TGC GAC TTT CCG CTG CGC TCG CAC CTT GAG CCC ACT AAC      622
Glu Gly Val Cys Asp Phe Pro Leu Arg Ser His Leu Glu Pro Thr Asn
            195                 200                 205

CAT GCC ATC ATT CAG ACG CTG ATG AAC TCC ATG GAC CCG GGC TCC ACC      670
His Ala Ile Ile Gln Thr Leu Met Asn Ser Met Asp Pro Gly Ser Thr
        210                 215                 220

CCG CCT AGC TGC TGC GTT CCC ACC AAA CTG ACT CCC ATT AGC ATC CTG      718
Pro Pro Ser Cys Cys Val Pro Thr Lys Leu Thr Pro Ile Ser Ile Leu
    225                 230                 235

TAC ATC GAC GCG GGC AAT AAT GTN GTC TAC AAG CAG TAT GAG GAC ATG      766
Tyr Ile Asp Ala Gly Asn Asn Xaa Val Tyr Lys Gln Tyr Glu Asp Met
240                 245                 250                 255

GTG GTG GAG TCC TGC GGC TGT AGG TAGCGGTGCT GTCCCGCCAC CTGGGCCAGG     820
Val Val Glu Ser Cys Gly Cys Arg
                260

GACCATGGAG GGAGGCCTGA CTGCCGAGAA AGGAGCAGGA GCTGGCCTTG GAAGAGGCCA    880

CAGGTGGGGG ACAGCCTGAA AGTAGGAGCA CAGTAAGAAG CAGCCCAGCC TTCCCAGAAC    940

CTTCCAATCC CCCAACCCAG AAGCAGCTAA GGGGTTTCAC AACTTTTGGC CTTGCCAGCC   1000

TGGAAAGACT AGACAAGAGG GATTCTTCTC TTTTTATTAT GGCTTG                  1046

(2) INFORMATION FOR SEQ ID NO: 32:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO: 32:

Arg Lys Gln Ala Cys Ile Pro Ala Gly Pro Thr Leu Arg Gly Ser Ser
1               5                   10                  15

Gly Thr Gln Pro Arg Pro Ala Gly Lys Ser Phe Asp Val Trp Gln Gly
            20                  25                  30

Leu Arg Pro Gln Pro Trp Lys Gln Leu Cys Leu Glu Leu Arg Ala Ala
        35                  40                  45

Trp Gly Glu Leu Asp Xaa Gly Asp Thr Gly Ala Arg Ala Arg Gly Pro
    50                  55                  60

Gln Gln Pro Pro Leu Asp Leu Arg Ser Leu Gly Phe Gly Arg Arg
65                  70                  75                  80

Val Arg Pro Pro Gln Glu Arg Ala Leu Leu Val Val Phe Thr Arg Ser
```

```
                    85                  90                  95
Gln Arg Lys Asn Leu Phe Thr Glu Met His Glu Gln Leu Gly Ser Ala
                100                 105                 110

Glu Ala Ala Gly Ala Glu Gly Ser Cys Pro Ala Pro Ser Gly Ser Pro
        115                 120                 125

Asp Thr Gly Ser Trp Leu Pro Ser Pro Gly Arg Arg Arg Arg Arg Thr
130                 135                 140

Ala Phe Ala Ser Arg His Gly Lys Arg His Gly Lys Lys Ser Arg Leu
145                 150                 155                 160

Arg Cys Ser Arg Lys Pro Leu His Val Asn Phe Lys Glu Leu Gly Trp
                165                 170                 175

Asp Asp Trp Ile Ile Ala Pro Leu Glu Tyr Glu Ala Tyr His Cys Glu
                180                 185                 190

Gly Val Cys Asp Phe Pro Leu Arg Ser His Leu Glu Pro Thr Asn His
            195                 200                 205

Ala Ile Ile Gln Thr Leu Met Asn Ser Met Asp Pro Gly Ser Thr Pro
210                 215                 220

Pro Ser Cys Cys Val Pro Thr Lys Leu Thr Pro Ile Ser Ile Leu Tyr
225                 230                 235                 240

Ile Asp Ala Gly Asn Asn Xaa Val Tyr Lys Gln Tyr Glu Asp Met Val
                245                 250                 255

Val Glu Ser Cys Gly Cys Arg
                260

(2) INFORMATION FOR SEQ ID NO: 33:

(i) SEQUENCE CHARACTERISTICS:
        (A) LENGTH: 1345 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: HUMAN V1-1

(ix) FEATURE:
        (A) NAME/KEY: CDS
        (B) LOCATION: 138..1301

(ix) FEATURE:
        (A) NAME/KEY: mat_peptide
        (B) LOCATION: 990..1301

(xi) SEQUENCE DESCRIPTION: SEQ ID NO: 33:

AACTATAGCA CCTGCAGTCC CTGGTCTTGG GTGTAGGGGT GCGCTCCTGG TCCCGCGGCT      60

CAGGGATATG CAGTGACCAA TGGGTTGTTG GCCTGATGGG ACTTTTGGCT TGCTAAACCA     120

AAGCTCGGTT CGGATAG CCC GGG CGA AGA CGT CCG CTG CTC TGG GCC AGG       170
                   Pro Gly Arg Arg Arg Pro Leu Leu Trp Ala Arg
                   -284            -280            -275

CTG GCA GCG TTC AGG CTG GGG CAG AGA CGC GGA GTC GGG CGC TGG CTC      218
Leu Ala Ala Phe Arg Leu Gly Gln Arg Arg Gly Val Gly Arg Trp Leu
        -270            -265            -260

CAA CAG GCC TGG CTC CCA CAT CGA AGA CAG CTG GGC CAT TTG CTG TTA      266
Gln Gln Ala Trp Leu Pro His Arg Arg Gln Leu Gly His Leu Leu Leu
        -255            -250            -245
```

-continued

```
GGA GGC CCC GCG CTG ACA GTG TGC AGG ATT TGC TCT TAC ACA GCT CTT        314
Gly Gly Pro Ala Leu Thr Val Cys Arg Ile Cys Ser Tyr Thr Ala Leu
            -240             -235             -230

TCT CTC TGT CCC TGC CGG TCC CCC GCA GAC GAA TCG GCA GCC GAA ACA        362
Ser Leu Cys Pro Cys Arg Ser Pro Ala Asp Glu Ser Ala Ala Glu Thr
-225             -220             -215             -210

GGC CAG AGC TTC CTG TTC GAC GTG TCC AGC CTT AAC GAC GCA GAC GAG        410
Gly Gln Ser Phe Leu Phe Asp Val Ser Ser Leu Asn Asp Ala Asp Glu
                -205             -200             -195

GTG GTG GGT GCC GAG CTG CGC GTG CTG CGC CGG GGA TCT CCA GAG TCG        458
Val Val Gly Ala Glu Leu Arg Val Leu Arg Arg Gly Ser Pro Glu Ser
            -190             -185             -180

GGC CCA GGC AGC TGG ACT TCT CCG CCG TTG CTG CTG TCC ACG TGC            506
Gly Pro Gly Ser Trp Thr Ser Pro Pro Leu Leu Leu Ser Thr Cys
        -175             -170             -165

CCG GGC GCC GCC CGA GCG CCA CGC CTG CTG TAC TCG CGG GCA GCT GAG        554
Pro Gly Ala Ala Arg Ala Pro Arg Leu Leu Tyr Ser Arg Ala Ala Glu
        -160             -155             -150

CCC CTA GTC GGT CAG CGC TGG GAG GCG TTC GAC GTG GCG GAC GCC ATG        602
Pro Leu Val Gly Gln Arg Trp Glu Ala Phe Asp Val Ala Asp Ala Met
-145             -140             -135             -130

AGG CGC CAC CGT CGT GAA CCG CGC CCC CCC CGC GCG TTC TGC CTC TTG        650
Arg Arg His Arg Arg Glu Pro Arg Pro Pro Arg Ala Phe Cys Leu Leu
                -125             -120             -115

CTG CGC GCA GTG GCA GGC CCG GTG CCG AGC CCG TTG GCA CTG CGG CGA        698
Leu Arg Ala Val Ala Gly Pro Val Pro Ser Pro Leu Ala Leu Arg Arg
            -110             -105             -100

CTG GGC TTC GGC TGG CCG GGC GGA GGG GGC TCT GCG GCA GAG GAG CGC        746
Leu Gly Phe Gly Trp Pro Gly Gly Gly Gly Ser Ala Ala Glu Glu Arg
        -95              -90              -85

GCG GTG CTA GTC GTC TCC TCC CGC ACG CAG AGG AAA GAG AGC TTA TTC        794
Ala Val Leu Val Val Ser Ser Arg Thr Gln Arg Lys Glu Ser Leu Phe
        -80              -75              -70

CGG GAG ATC CGC GCC CAG GCC CGC GCG CTC GGG GCC GCT CTG GCC TCA        842
Arg Glu Ile Arg Ala Gln Ala Arg Ala Leu Gly Ala Ala Leu Ala Ser
-65              -60              -55              -50

GAG CCG CTG CCC GAC CCA GGA ACC GGC ACC GCG TCG CCA AGG GCA GTC        890
Glu Pro Leu Pro Asp Pro Gly Thr Gly Thr Ala Ser Pro Arg Ala Val
                -45              -40              -35

ATT GGC GGC CGC AGA CGG AGG AGG ACG GCG TTG GCC GGG ACG CGG ACA        938
Ile Gly Gly Arg Arg Arg Arg Thr Ala Leu Ala Gly Thr Arg Thr
            -30              -25              -20

GCG CAG GGC AGC GGC GGG GGC GCG GGC CGG GGC CAC GGG CGC AGG GGC        986
Ala Gln Gly Ser Gly Gly Gly Ala Gly Arg Gly His Gly Arg Arg Gly
        -15              -10               -5

CGG AGC CGC TGC AGC CGC AAG CCG TTG CAC GTG GAC TTC AAG GAG CTC       1034
Arg Ser Arg Cys Ser Arg Lys Pro Leu His Val Asp Phe Lys Glu Leu
 1                5                10                15

GGC TGG GAC GAC TGG ATC ATC GCG CCG CTG GAC TAC GAG GCG TAC CAC       1082
Gly Trp Asp Asp Trp Ile Ile Ala Pro Leu Asp Tyr Glu Ala Tyr His
                 20               25                30

TGC GAG GGC CTT TGC GAC TTC CCT TTG CGT TCG CAC CTC GAG CCC ACC       1130
Cys Glu Gly Leu Cys Asp Phe Pro Leu Arg Ser His Leu Glu Pro Thr
             35               40               45

AAC CAT GCC ATC ATT CAG ACG CTG CTC AAC TCC ATG GCA CCA GAC GCG       1178
Asn His Ala Ile Ile Gln Thr Leu Leu Asn Ser Met Ala Pro Asp Ala
         50               55               60

GCG CCG GCC TCC TGC TGT GTG CCA GCG CGC CTC AGC CCC ATC AGC ATC       1226
Ala Pro Ala Ser Cys Cys Val Pro Ala Arg Leu Ser Pro Ile Ser Ile
 65               70               75
```

```
CTC TAC ATC GAC GCC GCC AAC AAC GTT GTC TAC AAG CAA TAC GAG GAC    1274
Leu Tyr Ile Asp Ala Ala Asn Asn Val Val Tyr Lys Gln Tyr Glu Asp
 80              85                  90                  95

ATG GTG GTG GAG GCC TGC GGC TGC AGG TAGCGCGCGG GCCGGGGAGG          1321
Met Val Val Glu Ala Cys Gly Cys Arg
                100

GGGCAGCCAC GCGGCCGAGG ATCC                                         1345
```

(2) INFORMATION FOR SEQ ID NO: 34:

(i) SEQUENCE CHARACTERISTICS:
        (A) LENGTH: 388 amino acids
        (B) TYPE: amino acid
        (D) TOPOLOGY: linear (ii) MOLECULE TYPE: protein (xi) SEQUENCE DESCRIPTION: SEQ ID NO: 34:

```
Pro Gly Arg Arg Arg Pro Leu Leu Trp Ala Arg Leu Ala Ala Phe Arg
-284            -280                -275                -270

Leu Gly Gln Arg Arg Gly Val Gly Arg Trp Leu Gln Gln Ala Trp Leu
        -265                -260                -255

Pro His Arg Arg Gln Leu Gly His Leu Leu Leu Gly Gly Pro Ala Leu
        -250                -245                -240

Thr Val Cys Arg Ile Cys Ser Tyr Thr Ala Leu Ser Leu Cys Pro Cys
        -235                -230                -225

Arg Ser Pro Ala Asp Glu Ser Ala Ala Glu Thr Gly Gln Ser Phe Leu
-220            -215                -210                -205

Phe Asp Val Ser Ser Leu Asn Asp Ala Asp Glu Val Val Gly Ala Glu
                -200                -195                -190

Leu Arg Val Leu Arg Arg Gly Ser Pro Glu Ser Gly Pro Gly Ser Trp
        -185                -180                -175

Thr Ser Pro Pro Leu Leu Leu Ser Thr Cys Pro Gly Ala Ala Arg
        -170                -165                -160

Ala Pro Arg Leu Leu Tyr Ser Arg Ala Ala Glu Pro Leu Val Gly Gln
        -155                -150                -145

Arg Trp Glu Ala Phe Asp Val Ala Asp Ala Met Arg Arg His Arg Arg
-140            -135                -130                -125

Glu Pro Arg Pro Pro Arg Ala Phe Cys Leu Leu Leu Arg Ala Val Ala
                -120                -115                -110

Gly Pro Val Pro Ser Pro Leu Ala Leu Arg Arg Leu Gly Phe Gly Trp
        -105                -100                 -95

Pro Gly Gly Gly Gly Ser Ala Ala Glu Glu Arg Ala Val Leu Val Val
         -90                 -85                 -80

Ser Ser Arg Thr Gln Arg Lys Glu Ser Leu Phe Arg Glu Ile Arg Ala
        -75                  -70                 -65

Gln Ala Arg Ala Leu Gly Ala Ala Leu Ala Ser Glu Pro Leu Pro Asp
-60              -55                 -50                 -45

Pro Gly Thr Gly Thr Ala Ser Pro Arg Ala Val Ile Gly Gly Arg Arg
                -40                 -35                 -30

Arg Arg Arg Thr Ala Leu Ala Gly Thr Arg Thr Ala Gln Gly Ser Gly
        -25                 -20                 -15

Gly Gly Ala Gly Arg Gly His Gly Arg Arg Gly Arg Ser Arg Cys Ser
        -10                  -5                   1

Arg Lys Pro Leu His Val Asp Phe Lys Glu Leu Gly Trp Asp Asp Trp
 5               10                  15                  20
```

-continued

```
Ile Ile Ala Pro Leu Asp Tyr Glu Ala Tyr His Cys Glu Gly Leu Cys
            25                  30                      35

Asp Phe Pro Leu Arg Ser His Leu Glu Pro Thr Asn His Ala Ile Ile
            40                  45                  50

Gln Thr Leu Leu Asn Ser Met Ala Pro Asp Ala Ala Pro Ala Ser Cys
        55                  60                  65

Cys Val Pro Ala Arg Leu Ser Pro Ile Ser Ile Leu Tyr Ile Asp Ala
        70                  75                  80

Ala Asn Asn Val Val Tyr Lys Gln Tyr Glu Asp Met Val Val Glu Ala
    85                  90                  95                  100

Cys Gly Cys Arg (2) INFORMATION FOR SEQ ID NO: 35:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: primer number 8

(xi) SEQUENCE DESCRIPTION: SEQ ID NO: 35:

TGTATGCGAC TTCCCGC                                              17
```